(12) United States Patent
Ainsworth et al.

(10) Patent No.: US 7,601,171 B2
(45) Date of Patent: Oct. 13, 2009

(54) SPINAL MOTION PRESERVATION ASSEMBLIES

(75) Inventors: Stephen D. Ainsworth, Wilmington, NC (US); Robert L. Assell, Wilmington, NC (US); Eugene A. Dickhudt, Lino Lakes, MN (US); Bradley J. Wessman, Wilmington, NC (US)

(73) Assignee: TranS1 Inc., Wilmington, NC (US)

( * ) Notice: Subject to any disclaimer, the term of this patent is extended or adjusted under 35 U.S.C. 154(b) by 431 days.

(21) Appl. No.: 11/256,810

(22) Filed: Oct. 24, 2005

(65) Prior Publication Data

US 2006/0079898 A1 Apr. 13, 2006

Related U.S. Application Data

(63) Continuation-in-part of application No. 11/199,541, filed on Aug. 8, 2005, and a continuation-in-part of application No. 10/972,184, filed on Oct. 22, 2004, and a continuation-in-part of application No. 10/972,039, filed on Oct. 22, 2004, now Pat. No. 7,491,236, and a continuation-in-part of application No. 10/972,040, filed on Oct. 22, 2004, now Pat. No. 7,547,324, and a continuation-in-part of application No. 10/972,176, filed on Oct. 22, 2004.

(60) Provisional application No. 60/621,148, filed on Oct. 22, 2004, provisional application No. 60/621,730, filed on Oct. 25, 2004, provisional application No. 60/558,069, filed on Mar. 31, 2004, provisional application No. 60/513,899, filed on Oct. 23, 2003, provisional application No. 60/599,989, filed on Aug. 9, 2004.

(51) Int. Cl.
  *A61F 2/44* (2006.01)
(52) U.S. Cl. .................................................. 623/17.11
(58) Field of Classification Search ................. 606/246, 606/257, 300, 301; 623/17.11–17.12; 403/138; 411/379–381, 384, 505–507, 383, 389, 392
See application file for complete search history.

(56) References Cited

U.S. PATENT DOCUMENTS

| 640,661 | A | * | 1/1900 | Johnstone | 411/380 |
|---|---|---|---|---|---|
| 1,029,104 | A | * | 6/1912 | Clark | 411/379 |
| 1,079,224 | A | * | 11/1913 | Dodds | 411/380 |
| 1,086,144 | A | * | 2/1914 | Dodds | 411/379 |
| 1,111,691 | A | * | 9/1914 | Flannery | 411/380 |
| 2,586,556 | A | | 2/1952 | Mullikin | |
| 3,272,541 | A | * | 9/1966 | Latzen | 403/138 |

(Continued)

FOREIGN PATENT DOCUMENTS

WO WO 9100713 A1 1/1991

*Primary Examiner*—Thomas C Barrett
*Assistant Examiner*—Nicholas Woodall
(74) *Attorney, Agent, or Firm*—The Eclipse Group LLP; Kevin E. Flynn

(57) ABSTRACT

Spinal motion preservation assemblies adapted for use in a spinal motion segment are disclosed including the process for delivering and assembling the spinal motion preservation assemblies in the spinal motion segment via an axial channel created with a trans-sacral approach. The spinal motion preservation assemblies make use of a dual pivot. A number of different embodiments of spinal motion preservation assemblies are disclosed which include at least one component adapted for elastic deformation under compressive loads. The disclosed mobility preservation assemblies provide for dynamic stabilization (DS) of the spinal motion segment.

22 Claims, 28 Drawing Sheets

U.S. PATENT DOCUMENTS

| | | | |
|---|---|---|---|
| 3,367,326 A | 2/1968 | Frazier | 606/86 A |
| 3,837,347 A | 9/1974 | Tower | |
| 4,175,555 A | 11/1979 | Herbert | 606/304 |
| 4,276,874 A | 7/1981 | Wolvek et al. | |
| 4,297,047 A * | 10/1981 | Farrant | 403/138 |
| 4,309,777 A | 1/1982 | Patil | |
| 4,636,217 A | 1/1987 | Ogilvie et al. | |
| 4,854,797 A | 8/1989 | Gourd | |
| 4,858,601 A | 8/1989 | Glisson | 128/92 R |
| 4,875,794 A * | 10/1989 | Kern, Jr. | 403/132 |
| 4,932,925 A * | 6/1990 | Roinestad et al. | 474/206 |
| 4,932,975 A | 6/1990 | Main et al. | 623/17.12 |
| 5,002,576 A | 3/1991 | Fuhrmann et al. | |
| 5,059,193 A | 10/1991 | Kuslich | |
| 5,061,137 A | 10/1991 | Gourd | |
| 5,102,276 A | 4/1992 | Gourd | |
| 5,108,430 A | 4/1992 | Ravo | |
| 5,246,458 A | 9/1993 | Graham | |
| 5,338,297 A | 8/1994 | Kocur et al. | |
| 5,360,430 A | 11/1994 | Lin | 606/247 |
| 5,433,739 A | 7/1995 | Sluijter et al. | 607/99 |
| 5,480,401 A | 1/1996 | Navas | 616/256 |
| 5,562,737 A | 10/1996 | Graf | 623/17.14 |
| 5,702,453 A | 12/1997 | Rabbe et al. | 623/17 |
| 5,733,284 A | 3/1998 | Martin | |
| 5,743,912 A | 4/1998 | Lehille et al. | |
| 5,827,285 A | 10/1998 | Bramlet | 606/60 |
| 6,056,749 A | 5/2000 | Kuslich | 606/86 A |
| 6,063,121 A | 5/2000 | Xavier et al. | 623/17.15 |
| 6,086,589 A | 7/2000 | Kuslich et al. | 606/247 |
| 6,093,205 A | 7/2000 | McLeod et al. | |
| 6,190,413 B1 | 2/2001 | Sutcliffe | |
| 6,235,043 B1 | 5/2001 | Reiley et al. | |
| 6,258,090 B1 | 7/2001 | Jackson | |
| 6,428,576 B1 | 8/2002 | Haldimann | 623/17.16 |
| 6,440,168 B1 | 8/2002 | Cauthen | |
| 6,506,194 B1 | 1/2003 | Hajianpour | |
| 6,558,390 B2 | 5/2003 | Cragg | 606/80 |
| 6,582,466 B1 | 6/2003 | Gauchet | |
| 6,582,468 B1 | 6/2003 | Gauchet | |
| 6,626,943 B2 | 9/2003 | Eberlein et al. | |
| 6,656,184 B1 | 12/2003 | White et al. | |
| 6,682,561 B2 | 1/2004 | Songer et al. | 623/17.11 |
| 6,692,495 B1 | 2/2004 | Zacouto | |
| 6,730,088 B2 | 5/2004 | Yeh | 606/61 |
| 6,733,532 B1 | 5/2004 | Gauchet et al. | |
| 6,764,489 B2 | 7/2004 | Feree | |
| 6,821,277 B2 | 11/2004 | Teitelbaum | |
| 6,899,716 B2 | 5/2005 | Cragg | 606/86 R |
| 6,899,719 B2 | 5/2005 | Reiley et al. | |
| 6,964,665 B2 | 11/2005 | Thomas et al. | |
| 7,048,717 B1 | 5/2006 | Frassica | |
| 7,077,865 B2 | 7/2006 | Bao et al. | |
| 7,156,877 B2 | 1/2007 | Lotz et al. | |
| 7,291,150 B2 | 11/2007 | Graf | |
| 7,361,192 B2 * | 4/2008 | Doty | 623/17.12 |
| 7,419,505 B2 | 9/2008 | Fleischmann et al. | 623/17.11 |
| 7,491,236 B2 | 2/2009 | Cragg et al. | 623/17.11 |
| 7,547,324 B2 | 6/2009 | Cragg et al. | |
| 2001/0021852 A1 | 9/2001 | Chappius | |
| 2002/0035400 A1 | 3/2002 | Bryan et al. | |
| 2002/0068975 A1 | 6/2002 | Teitelbaum et al. | |
| 2002/0198527 A1 | 12/2002 | Muckter | |
| 2003/0028193 A1 | 2/2003 | Weil et al. | |
| 2003/0055427 A1 | 3/2003 | Graf | 606/61 |
| 2003/0114930 A1 | 6/2003 | Lim et al. | 623/17.11 |
| 2003/0204261 A1 | 10/2003 | Eisermann et al. | |
| 2004/0083002 A1 | 4/2004 | Belef et al. | |
| 2004/0210227 A1 | 10/2004 | Trail et al. | |
| 2004/0230309 A1 | 11/2004 | DiMauro et al. | |
| 2005/0043796 A1 | 2/2005 | Grant et al. | |
| 2005/0113919 A1 | 5/2005 | Cragg et al. | 623/17.11 |
| 2005/0113929 A1 | 5/2005 | Cragg et al. | |
| 2005/0149191 A1 | 7/2005 | Cragg et al. | |
| 2005/0177167 A1 | 8/2005 | Muckter | |
| 2005/0277940 A1 | 12/2005 | Neff | |
| 2006/0085073 A1 | 4/2006 | Raiszadeh | |
| 2006/0229609 A1 | 10/2006 | Wang | 606/61 |
| 2007/0168042 A1 | 7/2007 | Hudgins et al. | |

\* cited by examiner

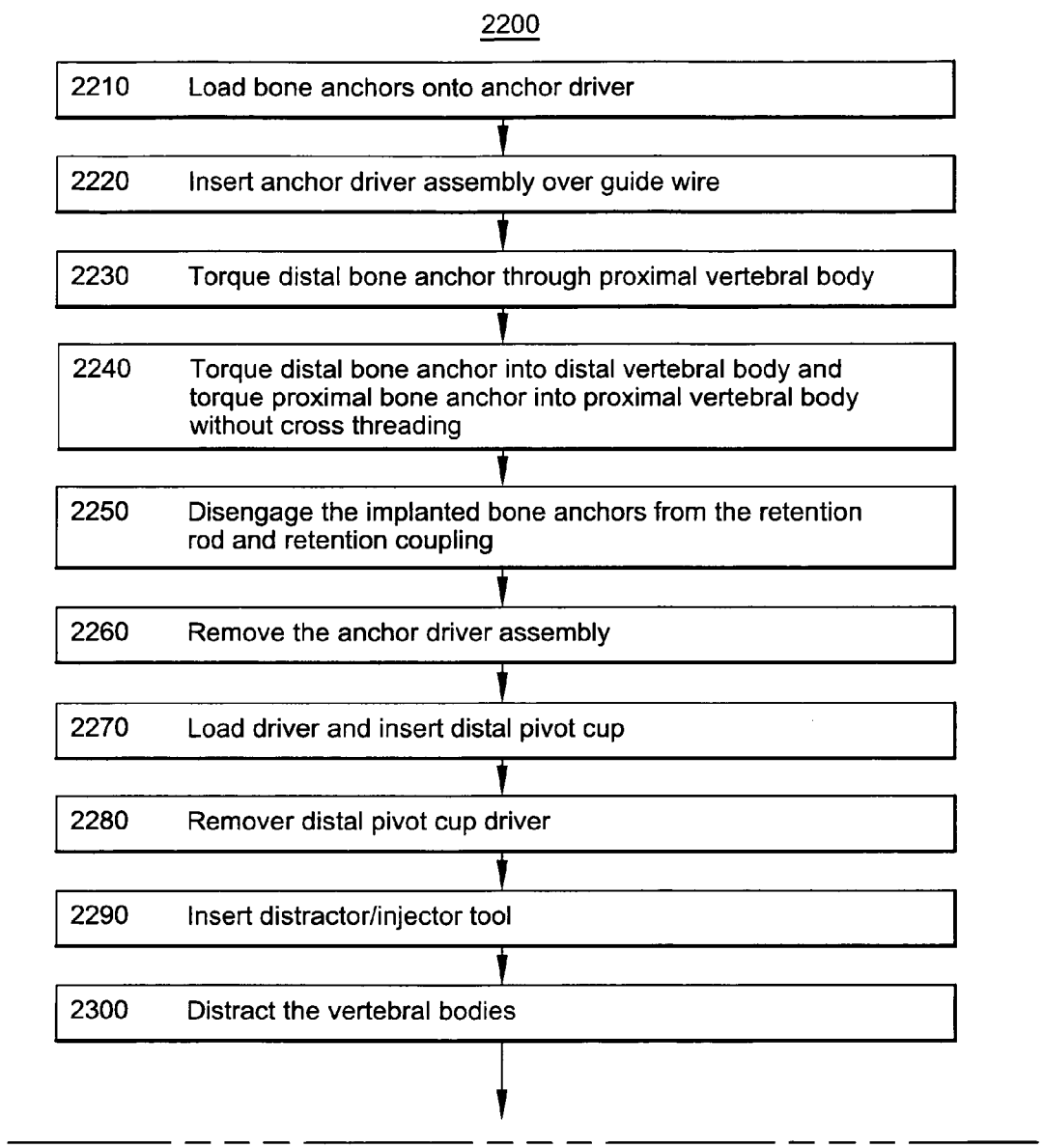

SPINAL MOTION PRESERVATION ASSEMBLIES

BACKGROUND OF THE INVENTION

This application claims priority and incorporates by reference a commonly assigned U.S. Provisional Application No. 60/621,148 filed Oct. 22, 2004 for Spinal Mobility Preservation Assemblies and second commonly assigned U.S. Provisional Application No. 60/621,730 filed Oct. 25, 2004 for Multi-Part Assembly for Introducing Axial Implants into the Spine. This application claims priority and incorporates by reference four co-pending and commonly assigned U.S. patent application Ser. Nos. 10/972,184, 10/927,039, 10/972,040, and 10/972,176 all filed on Oct. 22, 2004. These four applications claim priority to two provisional applications 60/558,069 filed Mar. 31, 2004 and 60/513,899 filed Oct. 23, 2003. Priority to these two provisionals is claimed through the four co-pending applications and the provisionals are incorporated by reference. This application also claims priority to co-pending and commonly assigned U.S. patent application Ser. No. 11/199,541 filed Aug. 8, 2005 and Provisional Application 60/599,989 filed Aug. 9, 2004 which is claimed as a priority document for the '541 application. Both of these applications are incorporated by reference.

This application extends the work done by TranS1 Inc. and incorporates by reference a set of United States applications, provisional applications, and issued patents including: 60/182,748 filed Feb. 16, 2000; Ser. No. 09/640,222 filed Aug. 16, 2000 (now issued as U.S. Pat. No. 6,575,979); Ser. No. 10/459,149 filed Jun. 11, 2003; Ser. No. 09/684,820 filed Oct. 10, 2000 (now issued as U.S. Pat. No. 6,558,386); Ser. No. 10/430,751 filed May 6, 2003; 60/182,748 filed Feb. 16, 2000; Ser. No. 09/782,583 filed Feb. 13, 2001 (issued as U.S. Pat. No. 6,558,390); Ser. No. 09/848,556 filed May 3, 2001; Ser. No. 10/125,771 filed Apr. 18, 2002 (issued as U.S. Pat. No. 6,899,716); Ser. No. 10/990,705 filed Nov. 17, 2004; Ser. No. 10/430,841 filed May 6, 2003; Ser. No. 09/710,369 filed Nov. 10, 2000 (issued as U.S. Pat. No. 6,740,090); Ser. No. 10/853,476 filed May 25, 2004; Ser. No. 09/709,105 filed Nov. 10, 2000 (issued as U.S. Pat. No. 6,790,210); Ser. No. 09/782,534 filed Feb. 13, 2001; application Ser. Nos. 10/971,779, 10/971,781, 10/971,731, 10/972,077, 10/971,765, 10/972,065, 10/971,775, 10/971,299, 10/971,780, all filed Oct. 22, 2004; 60/706,704 filed Aug. 9, 2005; Ser. No. 11/189,943 filed Jul. 26, 2005, Ser. No. 10/309,416 now U.S. Pat. No. 6,921,403 filed Dec. 3, 2002., While these applications have been incorporated by reference to provide additional detail it should be noted that these other applications (including those that have subsequently issued as patents) were written at an earlier time and had a different focus from the present application. Thus, to the extent that the teachings or use of terminology differs in any of these incorporated applications from the present application, the present application controls.

FIELD OF THE INVENTION

The present invention relates generally to implantable device assemblies, instrumentation systems, and methods for accessing and a spinal motion segment via a minimally-invasive trans-sacral approach (as described in U.S. Pat. No. 6,558,390 which is incorporated herein by reference) and procedures comprising the deployment of implantable components and assemblies that are anchored in bone that can be used to position, manage motion, and stabilize a vertebral motion segments in the human spine to relieve lower back pain, restore physiological function of the lumbar spine, and prevent progression or transition of degenerative disease. More specifically, the present invention generally relates to spinal motion preservation assemblies (MPA) generally introduced percutaneously through tissue to an access point on the spine in a minimally invasive, low trauma manner, to provide therapy to the spine.

BACKGROUND OF THE INVENTION

Overview

The present invention is an extension of work assigned to TranS1 Inc. with a principle place of business located in Wilmington, N.C. Much of the work is described in great detail in the many applications referenced above and incorporated by reference into this application. Accordingly, the background of the invention provided here does not repeat all of the detail provided in the earlier applications, but instead highlights how the present invention adds to this body of work.

The spinal column is a complex system of bone segments (vertebral bodies and other bone segments) which are in most cases separated from one another by discs in the intervertebral spaces (sacral vertebrae are an exception). FIG. 1 shows the various segments of a human spinal column as viewed from the side. In the context of the present invention, a "motion segment" comprises adjacent vertebrae, i.e., an inferior and a superior vertebral body, and the intervertebral disc space separating said two vertebral bodies, whether denucleated space or with intact or damaged spinal discs. Each motion segment contributes to the overall flexibility of the spine contributes to the overall ability of the spine to flex to provide support for the movement of the trunk and head.

The vertebrae of the spinal cord are conventionally subdivided into several sections. Moving from the head to the tailbone, the sections are cervical 104, thoracic 108, lumbar 112, sacral 116, and coccygeal 120. The individual vertebral bodies within the sections are identified by number starting at the vertebral body closest to the head. Of particular interest in this application are the vertebral bodies in the lumbar section and the sacral section. As the various vertebral bodies in the sacral section are usually fused together in adults, it is sufficient and perhaps more descriptive to merely refer to the sacrum rather than the individual sacral components.

It is useful to set forth some of the standard medical vocabulary before getting into a more detailed discussion of the background of the present invention. In the context of the this discussion: anterior refers to in front of the spinal column; (ventral) and posterior refers to behind the column (dorsal); cephalad means towards the patient's head (sometimes "superior"); caudal (sometimes "inferior") refers to the direction or location that is closer to the feet. As the present application contemplates accessing the various vertebral bodies and intervertebral spaces through a preferred approach that comes in from the sacrum and moves towards the head, proximal and distal are defined in context of this channel of approach. Consequently, proximal is closer to the beginning of the channel and thus towards the feet or the surgeon, distal is further from the beginning of the channel and thus towards the head, or more distant from the surgeon.

The individual motion segments within the spinal columns allow movement within constrained limits and provide protection for the spinal cord. The discs are important to bear and distribute the large forces that pass through the spinal column as a person walks, bends, lifts, or otherwise moves. Unfortunately, for a number of reasons referenced below, for some people, one or more discs in the spinal column will not operate as intended. The reasons for disc problems range from a congenital defect, disease, injury, or degeneration attributable to aging. Often when the discs are not operating properly, the gap between adjacent vertebral bodies is reduced and this causes additional problems including pain.

There are currently over 700,000 surgical procedures performed annually to treat lower back pain in the U.S. In 2004, it is conservatively estimated that there will be more than 200,000 lumbar fusions performed in the U.S., and more than 300,000 worldwide, representing approximately a $1 B endeavor in an attempt to alleviate patients' pain. Approximately 60% of spinal surgery takes place in the lumbar spine, and of that portion approximately 80% involves the lower lumbar vertebrae designated as the fourth lumbar vertebra ("L4"), the fifth lumbar vertebra ("L5"), and the first sacral vertebra ("S1"). Persistent low back pain is often attributable to degeneration of the disc between L5 and S1. (See edge between the lumbar region 112 and the sacrum 116 in FIG. 1).

A range of therapies have been developed to alleviate the pain associated with disc problems. One class of solutions is to remove the failed disc and then fuse the two adjacent vertebral bodies together with a permanent but inflexible spacing, also referred to as static stabilization. As mentioned above, an estimated 300,000 fusion operations take place each year. Fusing one section together ends the ability to flex in that motion segment. While the loss of the normal physiologic disc function for a motion segment through fusion of a motion segment may be better than continuing to suffer from the pain, it would be better to alleviate the pain and yet retain all or much of the normal performance of a healthy motion segment.

Another class of therapies attempts to repair the disc so that it resumes operation with the intended intervertebral spacing and mechanical properties. One type of repair is the replacement of the original damaged disc with a prosthetic disc. This type of therapy is called by different names such as dynamic stabilization or spinal motion preservation.

The Operation of the Spine

The bodies of successive lumbar, thoracic and cervical vertebrae articulate with one another and are separated by the intervertebral spinal discs. Each spinal disc comprises a fibrous cartilage shell enclosing a central mass, the "nucleus pulposus" (or "nucleus" herein) that provides for cushioning and dampening of compressive forces to the spinal column. The shell enclosing the nucleus comprises cartilaginous endplates adhered to the opposed cortical bone endplates of the cephalad and caudal vertebral bodies and the "annulus fibrosus" (or "annulus" herein) comprising multiple layers of opposing collagen fibers running circumferentially around the nucleus pulposus and connecting the cartilaginous endplates. The natural, physiological nucleus is comprised of hydrophilic (water attracting) mucopolysacharides and fibrous strands (protein polymers). The nucleus is relatively inelastic, but the annulus can bulge outward slightly to accommodate loads axially applied to the spinal motion segment.

The intervertebral discs are anterior to the spinal canal and located between the opposed end faces or endplates of a cephalad and a caudal vertebral bodies. The inferior articular processes articulate with the superior articular processes of the next succeeding vertebra in the caudal (i.e., toward the feet or inferior) direction. Several ligaments (supraspinous, interspinous, anterior and posterior longitudinal, and the ligamenta flava) hold the vertebrae in position yet permit a limited degree of movement. The assembly of two vertebral bodies, the interposed, intervertebral, spinal disc and the attached ligaments, muscles and facet joints is referred to as a "spinal motion segment".

The relatively large vertebral bodies located in the anterior portion of the spine and the intervertebral discs provide the majority of the weight bearing support of the vertebral column. Each vertebral body has relatively strong, cortical bone layer comprising the exposed outside surface of the body, including the endplates, and weaker, cancellous bone comprising the center of the vertebral body.

The nucleus pulposus that forms the center portion of the intervertebral disc consists of 80% water that is absorbed by the proteoglycans in a healthy adult spine. With aging, the nucleus becomes less fluid and more viscous and sometimes even dehydrates and contracts (sometimes referred to as "isolated disc resorption") causing severe pain in many instances. The spinal discs serve as "dampeners" between each vertebral body that minimize the impact of movement on the spinal column, and disc degeneration, marked by a decrease in water content within the nucleus, renders discs ineffective in transferring loads to the annulus layers. In addition, the annulus tends to thicken, desiccate, and become more rigid, lessening its ability to elastically deform under load and making it susceptible to fracturing or fissuring, and one form of degeneration of the disc thus occurs when the annulus fissures or is torn. The fissure may or may not be accompanied by extrusion of nucleus material into and beyond the annulus. The fissure itself may be the sole morphological change, above and beyond generalized degenerative changes in the connective tissue of the disc, and disc fissures can nevertheless be painful and debilitating. Biochemicals contained within the nucleus are enabled to escape through the fissure and irritate nearby structures.

A fissure also may be associated with a herniation or rupture of the annulus causing the nucleus to bulge outward or extrude out through the fissure and impinge upon the spinal column or nerves (a "ruptured" or "slipped" disc). With a contained disc herniation, the nucleus may work its way partly through the annulus but is still contained within the annulus or beneath the posterior longitudinal ligament, and there are no free nucleus fragments in the spinal canal. Nevertheless, even a contained disc herniation is problematic because the outward protrusion can press on the spinal cord or on spinal nerves causing sciatica.

Another disc problem occurs when the disc bulges outward circumferentially in all directions and not just in one location. This occurs when, over time, the disc weakens bulges outward and takes on a "roll" shape. Mechanical stiffness of the joint is reduced and the spinal motion segment may become unstable, shortening the spinal cord segment. As the disc "roll" extends beyond the normal circumference, the disc height may be compromised, and foramina with nerve roots are compressed causing pain. Current treatment methods other than spinal fusion for symptomatic disc rolls and herniated discs include "laminectomy" which involves the surgical exposure of the annulus and surgical excision of the symptomatic portion of the herniated disc followed by a relatively lengthy recuperation period. In addition, osteophytes may form on the outer surface of the disc roll and further encroach on the spinal canal and foramina through which nerves pass. The cephalad vertebra may eventually settle on top of the caudal vertebra. This condition is called "lumbar spondylosis".

Various other surgical treatments that attempt to preserve the intervertebral spinal disc and to simply relieve pain include a "discectomy" or "disc decompression" to remove some or most of the interior nucleus thereby decompressing and decreasing outward pressure on the annulus. In less invasive microsurgical procedures known as "microlumbar discectomy" and "automated percutaneous lumbar discectomy", the nucleus is removed by suction through a needle laterally extended through the annulus. Although these procedures are less invasive than open surgery, they nevertheless suffer the possibility of injury to the nerve root and dural sac, perineural scar formation, re-herniation of the site of the surgery, and instability due to excess bone removal. In addition, they generally involve the perforation of the annulus.

Although damaged discs and vertebral bodies can be identified with sophisticated diagnostic imaging, existing surgical interventions and clinical outcomes are not consistently satisfactory. Furthermore, patients undergoing such fusion surgery experience significant complications and uncomfortable, prolonged convalescence. Surgical complications include disc space infection; nerve root injury; hematoma formation; instability of adjacent vertebrae, and disruption of muscle, tendons, and ligaments, for example.

Several companies are pursuing the development of prosthesis for the human spine, intended to completely replace a physiological disc, i.e., an artificial disc. In individuals where the degree of degeneration has not progressed to destruction of the annulus, rather than a total artificial disc replacement, a preferred treatment option may be to replace or augment the nucleus pulposus, involving the deployment of a prosthetic disc nucleus. As noted previously, the normal nucleus is contained within the space bounded by the bony vertebrae above and below it and the annulus fibrosus, which circumferentially surrounds it. In this way the nucleus is completely encapsulated and sealed with the only communication to the body being a fluid exchange that takes place through the bone interface with the vertebrae, known as the endplates.

The hydroscopic material comprising the physiological nucleus has an affinity for water (and swells in volume) which is sufficiently powerful to distract (i.e., elevate or "inflate") the intervertebral disc space, despite the significant physiological loads that are carried across the disc in normal activities. These forces, which range from about 0.4× to about 1.8× body weight, generate local pressure well above normal blood pressure, and the nucleus and inner annulus tissue are, in fact, effectively avascular.

The existence of the nucleus as a cushion (e.g., the nucleus is the "air" in the "tire" known as a spinal disc), and the annulus, as a flexible member, contributes to the range of motion in the normal disc. Range of motion is described in terms of degrees of freedom (i.e., translation and rotation about three orthogonal planes relative to a reference point, the instantaneous center of rotation around the vertical axis of the spine). The advantages of axial spinal implant assemblies of the present invention in preserving, restoring, and/or managing mobility in terms of flexion, extension, compression, left/right (L/R) rotation, L/R lateral bending, and distraction will become more apparent from the description of the relationship between movement and anatomical structures of the spine, and the consequences and impact of injury (e.g., trauma/mechanical injury or aging) noted below.

Flexion and Extension

Flexion and extension of the spine combine forward sliding and rotation of the vertebrae. The facet joints and the annulus resist the forward sliding. Rotation is resisted by the annulus; capsules of the facet joints; action of the back muscles, and passive tension generated by the thoracolumbar fascia. Extension is resisted by the facet joints, and secondarily by the annulus.

The spine is resistant to injury if the force is only in pure flexion, as the combination of the facet joints and disc are intrinsically stable in this plane. While the spinal muscles can be injured during forceful flexion since they are important in controlling this motion, ensuing pain is not typically chronic.

Extension is impaired by impaction of the facet joints and eventually the inferior articular process against the lamina. This can result in a cartilage injury of the facet joint; disruption of the facet capsule, and facet joint or pars interarticularis fracture.

Compression

Compression of the spine is due to body weight and loads applied to the spine. Body weight is a minor compressive load. The major compressive load on the spine is produced by the back muscles. As a person bends forward, the body weight plus an external load must be balanced by the force generated by the back muscles. That is, muscle loads balance gravitational loads so that the spine is in equilibrium, to help keep us from falling over. The external force is calculated by multiplying the load times the perpendicular distance of the load from the spine. The greater the distance from the spine, the larger is the load. Since the back muscles act close to the spine, they must exert large forces to balance the load. The force generated by the back muscles results in compression of spinal structures.

Most of the compressive loads (~80%) are sustained by the anterior column (disc and vertebral body). The disc is a hydrostatic system. The nucleus acts as a confined fluid within the annulus. It converts compressive on the vertebral end plates (axial loads) into tension on the annulus fibers.

Compression injuries occur by two main mechanisms; axial loading by gravity or by muscle action. Gravitational injuries result from a fall onto the buttocks while muscular injuries result from severe exertion during pulling or lifting. A serious consequence of the injury is a fracture of the vertebral end plate. Since the end plate is critical to disc nutrition, an injury can change the biochemical and metabolic state of the disc. If the end plate heals, the disc may suffer no malice. However, if the end plate does not heal, the nucleus can undergo harmful changes. The nucleus loses its proteoglycans and thus its water-binding capacity. The hydrostatic properties of the nucleus are compromised. Instead of sharing the load between the nucleus and the annulus, more of the load is transferred to the annulus. The annulus fibers then fail. In addition to annular tears, the layers of the annular separate (delaminate). The disc may collapse or it may maintain its height with progressive annular tearing. If the annulus is significantly weakened, there may be a rupture of the disc whereby the nuclear material migrates into the annulus or into the spinal canal causing nerve root compression.

Rotation

Rotation of the spine is accomplished by the contraction of the abdominal muscles acting through the thorax and the thoracolumbar fascia. There are no primary muscles responsible for lumbar rotation. The facet joints and the collagen fibers of the annulus resist this rotation. In rotation, only 50% of the collagen fibers are in tension at any time, which renders the annulus susceptible to injury.

The spine is particularly susceptible to injury in a loading combination of rotation and flexion. Flexion pre-stresses the annular fibers. As the spine rotates, compression occurs on the facet joint surfaces of the joint opposite the rotation. Distraction occurs on the facet joint on the same side of the rotation. The center of rotation of the motion segment shifts from the back of the disc to the facet joint in compression. The disc shifts sideways and shear forces on the annular fibers are significant. Since the annular fibers are weak in this direction, they can tear. If the rotation continues, the facet joints can sustain cartilage injury, fracture, and capsular tears while the annulus can tear in several different ways. Any of these injuries can be a source of pain.

Lateral Bending

Bending is a combination of lateral flexion and rotation through the annulus and facet joints.

Distraction

Pure distraction rarely occurs and is usually a combination of tension and compression on the spinal joints depending on the direction of applied force. An example of a distraction force is therapeutic spinal traction to "unload" the spine.

In the context of the present invention, as used herein the term distraction refers procedurally to an elevation in height that increases the intervertebral disc space resulting from introduction of the motion preservation assembly or prosthetic nucleus device ("PND"), which may be achieved either in the axial deployment of the device itself, or assisted by means of a temporary distraction rod, during implantation. Temporary distraction refers to elevation of disc height by means, such as a distraction rod, which is subsequently removed but wherein the elevation is retained intra-operatively, while the patient remains prone. Thus, the device may be inserted into an elevated disc space first created by other distraction means, and thereafter physical presence and dimensionality of the inserted device is key to preserving that height space, to decompress the disc and alleviate pain caused by nerve impingement.

Thus if one takes a reference point at the top face of a vertebral body, the motion segment comprising that vertebral body, the next most cephalad vertebral body, and the intervertebral disc between those two vertebral bodies has six degrees of freedom. If the x axis is aligned with the anterior/posterior direction, and the y axis is aligned with the right/and left side, and the z axis aligned with the caudal/cephalad direction then the six degrees of freedom are as follows:

| | | |
|---|---|---|
| Translation along | X axis | Movement of upper vertebral body in anterior/posterior direction |
| Translation along | Y axis | Movement of upper vertebral body to right or to left |
| Translation along | Z axis | Movement of upper vertebral body away from lower vertebral body (distraction) or towards lower vertebral body compression. |
| Rotation in plane defined by | X and Y | Rotation of spine clockwise or counterclockwise |
| Rotation in plane defined by | X and Z | Rotation of spine to flex or extend the spine |
| Rotation in plane defined by | Y and Z | Rotation of spine to move laterally to right or left |

To date, drawbacks of currently contemplated or deployed prosthetic nucleus devices include subsidence; their tendency to extrude or migrate; to erode the bone; to degrade with time, or to fail to provide sufficient biomechanical load distribution and support. Some of these drawbacks relate to the fact that their deployment typically involves a virtually complete discectomy of the disc achieved by instruments introduced laterally through the patient's body to the disc site and manipulated to cut away or drill lateral holes through the disc and adjoining cortical bone. The endplates of the vertebral bodies, which comprise very hard cortical bone and help to give the vertebral bodies needed strength, are usually weakened or destroyed during the drilling. The vertebral endplates are special cartilage structures that surround the top and bottom of each vertebra and are in direct contact with the disc. They are important to the nutrition of the disc because they allow the passage of nutrients and water into the disc. If these structures are injured, it can lead to deterioration of the disc and altered disc function. Not only do the large laterally drilled hole or holes compromise the integrity of the vertebral bodies, but the spinal cord can be injured if they are drilled too posterior.

Alternatively, current devices are sometimes deployed through a surgically created or enlarged hole in the annulus. The annulus fibrosus consists of tough, thick collagen fibers. The collagen fibers which comprise the annulus fibrosus are arranged in concentric, alternating layers. Intra-layer orientation of these fibers is parallel, however, each alternating (i.e., interlayer) layers' collagen fibers are oriented obliquely (~120). This oblique orientation allows the annulus to resist forces in both vertical and horizontal directions. Axial compression of a disc results in increased pressure in the disc space. This pressure is transferred to the annulus in the form of loads (stresses) perpendicular to the wall of the annulus. With applied stress, these fibrous layers are put in tension and the angle from horizontal decreases to better resist the load, i.e., the annulus works to resist these perpendicular stresses by transferring the loads around the circumference of the annulus (Hoop Stress). Vertical tension resists bending and distraction (flexion and extension). Horizontal tension resists rotation and sliding (i.e., twisting). While the vertical components of the annulus' layers enable the disc to withstand forward and backward bending well, only half of the horizontal fibers of the annulus are engaged during a rotational movement. In general, the disc is more susceptible to injury during a twisting motion, deriving its primary protection during rotation from the posterior facet joints; however, this risk is even greater if and when the annulus is compromised.

Moreover, annulus disruption will remain post-operatively, and present a pathway for device extrusion and migration in addition to compromising the physiological biomechanics of the disc structure. Other devices, in an attempt to provide sufficient mechanical integrity to withstand the stresses to which they will be subjected, are configured to be so firm, stiff, and inflexible that they tend to erode the bone or become imbedded, over time, in the vertebral bodies, a phenomenon known as "subsidence", sometimes also termed "telescoping". The result of subsidence is that the effective length of the vertebral column is shortened, which can subsequently cause damage to the nerve root and nerves that pass between the two adjacent vertebrae.

SUMMARY OF THE DISCLOSURE

Spinal mobility preservation assemblies are disclosed which are configured to comprise a plurality of pivots, that function in conjunction with one or more elastomeric (e.g., semi-compliant; compressible) or spring component (including non-helical springs such as the relatively flat Belleville disc), that are particularly effective in preserving motion in any plane relative to the longitudinal axis of the spine.

In the context of the present invention, "planes" are defined relative to x,y,z orthogonal axes, where z is the longitudinal axis of the spine. More specifically, rotation about x,y,z and motion about x,y are enabled by a plurality of unconstrained pivot points, and the elastomeric component enables motion in the z direction and serves to dampen axial compression.

As used herein, the term unconstrained refers to the fact that pivots are not fixed, and refers to motion that exceeds the normal range of motion in all six degrees of freedom. Thus, with respect to the lumbar spine, whereas the normal full range of motion typically allows for about 12 degrees of flexion, about 8 degrees of extension, about 9 degrees of left or right lateral bend, and about 2 degrees of clockwise or counterclockwise motion, the mobility preservation assemblies in accordance with a preferred aspect of the present invention (e.g., with unconstrained dual-pivots in conjunction with an elastomeric component) which have been configured for the lumbar spine generally will permit at least about 4 degrees, often at least about 8 degrees and preferably no more than about 20 degrees of flexion (bending forwards), and at least about 4 degrees, often at least about 6 degrees and preferably no more than about 20 degrees of extension (bending backwards). Rotation is completely unconstrained, with no limitation. With respect to the spine generally, MPA in accordance with the invention generally will often provide at least about 100 or 125% of the normal full range of motion for any particular motion segment being treated.

While it is known in the art to implant certain other human joints (e.g., fingers and knees) with devices meant to preserve translation, the spine is the only articulating human joint with six degrees of freedom with respect to motion, as described above. Unlike current devices (e.g., Medtronic® Maverick™ device, or the SpineCore Flexicore™ intervertebral disc), the spinal implant assemblies of the present invention are able to preserve motion (including translation) in all six degrees of freedom. This is because these assemblies are configured with a plurality of pivot points preferably in conjunction with an elastomeric or otherwise elastically deformable component, so as not to impede the motion (translation), in any plane, of natural structures which bear physiologic loads, and their deployment in an orientation in approximately the line of principal compressive stress, i.e., placement at approximately the center of rotation vis à vis a human disc motion segment.

Generally, the assemblies may be inserted axially within the spine, following either partial or complete nucleectomy and through a cannula that is docked against the sacrum, into a surgically de-nucleated disc space, from said access point across a treatment zone. In one aspect of the invention, prosthetic or augmentation materials are introduced, through at least one vertebral body or into at least one disc space. The introduction of the spinal MPA of the present invention is accomplished without the need to surgically create or deleteriously enlarge an existing hole in the annulus fibrosus of the disc, and their deployment therapeutically preserves the physiological function of natural disc structures.

In one aspect of the invention, risks associated with implant expulsion, migration, or subsidence (that are inherently less for the MPA of the present invention) may be even further mitigated by retention means, e.g., by external, self-tapping threads configured to distribute stress evenly over a large surface area, that engage the vertebral body and secure (i.e., anchor) the implant assemblies therein.

The screw threads are typical of "cancellous" type bone threads known in the art. The threads are typically cut with generally flat faces on the flights of the thread with the most flat of the faces oriented in the direction of the applied load. In one embodiment, the thread profile generally comprises deep flights with an asymmetric thread form, which provides the advantage of improved weight bearing and load distribution. Threads are formed on root portions and extend as continuous threads from the trailing end to the leading end of the respective threaded sections. The screw threads include multiple revolutions that are spaced apart along the roots by inter-thread spacings. The proximal component and distal component threads are like-handed (i.e. the threads turn in the same direction) so that both screw threads are right-handed or so that both are left-handed.

The self-tapping threads may or may not be configured to assist in distraction of adjacent vertebral bodies within a motion segment, i.e., may or may not be configured with distal and proximal components (anchored in superior and inferior vertebral bodies, respectively) with differential thread pitches, and wherein the distal anchor has a major diameter that is less than that of the proximal anchor. Clockwise rotation of embodiments configured with right-handed threads (i.e., differential pitch and major diameters as just described) advances assemblies axially and distracts the superior and inferior vertebral bodies within a motion segment relative one to the other.

In the context of the present invention, "dynamic" refers to non-static devices with an inherent ability to allow mobility by enabling or facilitating forces or load bearing that assist or substitute for physiological structures that are otherwise compromised, weakened or absent. The mobility preservation assemblies (MPA) of the present invention provide dynamic stabilization (DS) across a progression-of-treatment interventions for treating symptomatic discogenic pain, ranging from treatment in patients where little degeneration or collapse is evident radio-graphically, to those for whom prosthetic nucleus devices or total disc replacements are indicated. For example, a prosthetic nucleus (PN) would be indicated in patients with a greater degree of degeneration and loss of disc height but not to the stage where advanced annular break-down is present. A prosthetic nucleus would go beyond dynamic stabilization by including an aggressive nucleectomy and subsequent filling of the de-nucleated space with an appropriate material. Here, the goal is to restore disc height and motion. Total disc replacement (TDR) are generally indicated with more advanced disease than with a prosthetic nucleus but where some annular function remains. The motion preservation assemblies of the present invention serve as prosthetic disc replacements (PDR) that are much less invasive (in terms of deployment) than traditional total disc replacements, and are configured so as to augment, preserve, restore, and/or manage the physiological function according to the intervention indicated. In general, the axial motion preservation assemblies of the present invention disclosed herein are preferably configured as devices with an aspect ratio of greater than 1, i.e., the device dimension in the axial vertebral plane is greater than the device dimension in any orthogonal direction to that axial plane in close proximity to the physiological instantaneous center of axial rotation, and are deployed in an orientation in approximately the line of principal compressive stress, and placed at approximately the center of rotation vis à vis a human disc motion segment.

DETAILED DESCRIPTION

Axial Trans-Sacral Access

The present invention contemplates the use of the axial trans-sacral access to the lumbo-sacral spine. The axial trans-sacral access method illustrated in FIG. 2, eliminates the need for muscular dissection and other invasive steps associated with traditional spinal surgery while allowing for the design and deployment of new and improved instruments and therapeutic interventions, including stabilization, motion preservation, and fixation devices/fusion systems across a progression-of-treatment in intervention.

Figure 2A:
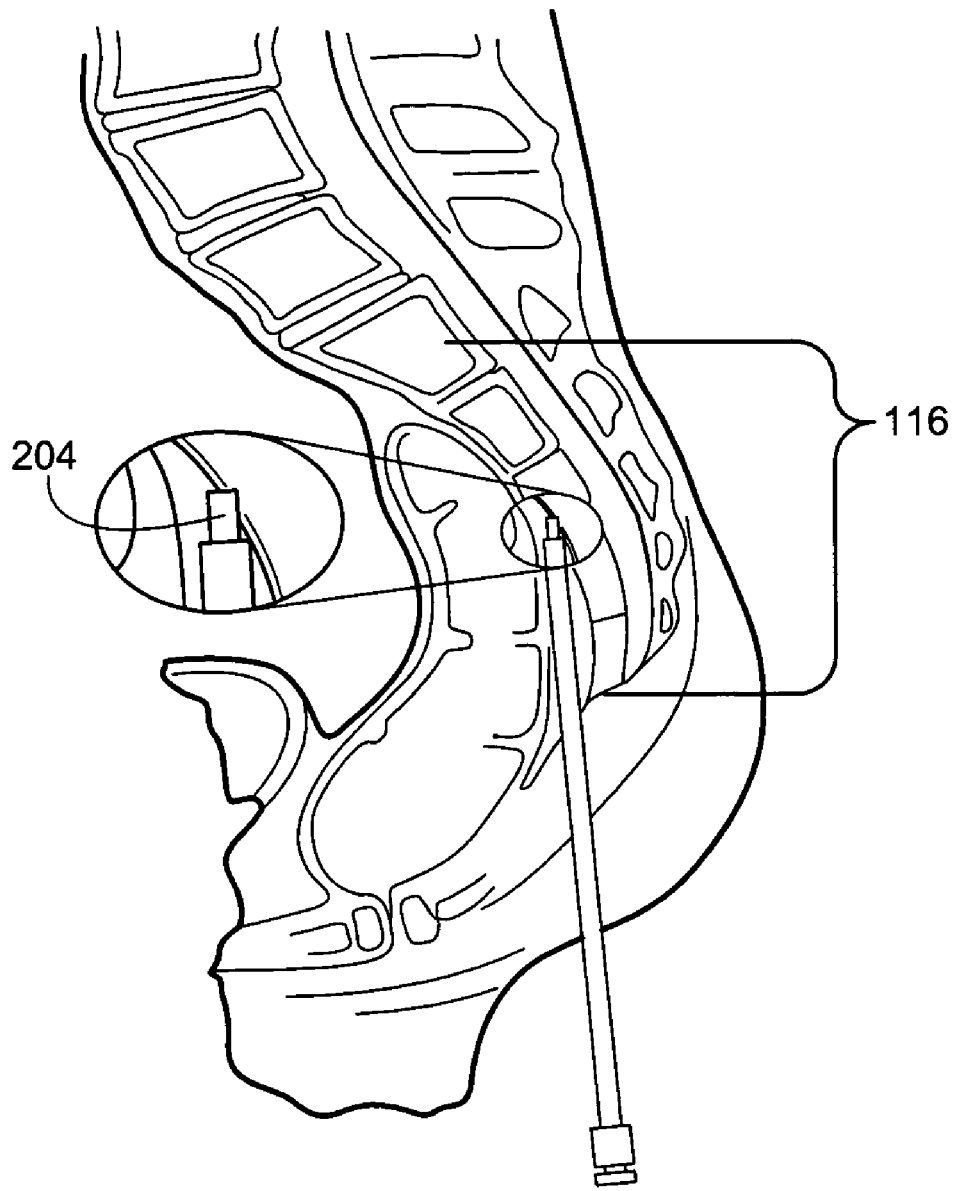
FIG. 2 illustrates an anterior axial trans-sacral access method of creating an axial channel in the spine which can be used to prepare an axial channel in the spine for use with the present invention.
Figure 2B:
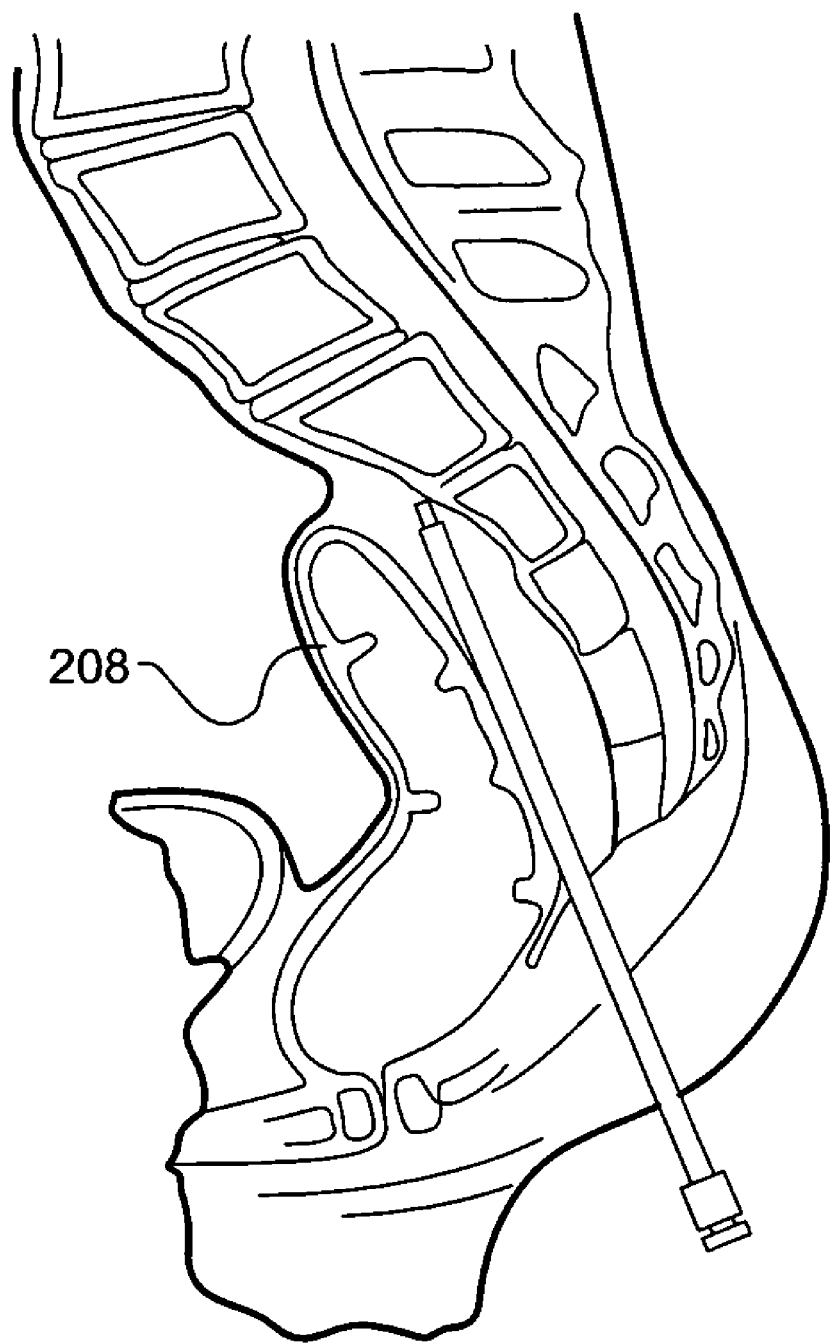
Figure 2C:
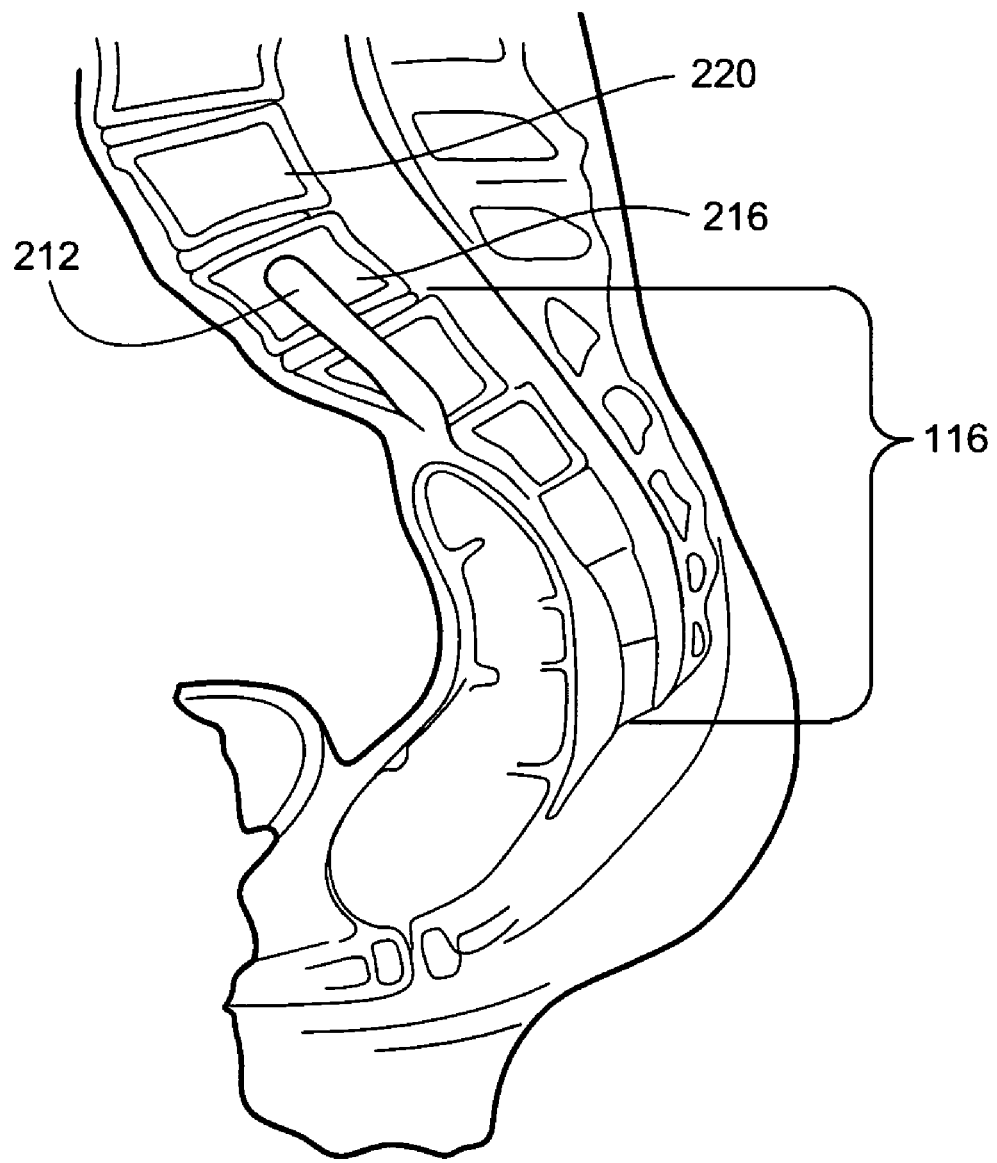

FIG. 2 provides an introductory overview of the process with FIGS. 2A and 2B showing the process of "walking" a blunt tip stylet 204 up the anterior face of the sacrum 116 to the desired position on the sacrum 116 while monitored on a fluoroscope (not shown). This process moves the rectum 208 out of the way so that a straight path is established for the subsequent steps. FIG. 2C illustrates a representative axial trans-sacral channel 212 established through the sacrum 116, the L5/sacrum intervertebral space, the L5 vertebra 216, the L4/L5 intervertebral space, and into the L4 vertebra 220. If therapy is not being provided to the L4/L5 motion segment then the channel would end in L5 rather than extend into L4.

The discussion of FIG. 2 is provided to provide context for the present invention. Previous applications (some now issued as United States patents) assigned to TranS1, Inc. have included a description of an alternative access method that is a posterior trans-sacral axial spinal approach rather than an anterior trans-sacral axial spinal approach. (See e.g. U.S. Pat. No. 6,558,386 for Axial Spinal Implant and Method and Apparatus for Implanting an Axial Spinal Implant Within the Vertebrae of the Spine as this patent describes the anterior trans-sacral axial approach illustrated in FIG. 2 and is incorporated by reference in its entirety.) The teachings of the present invention can be utilized with an axial trans-sacral channel.

A brief overview of this method of accessing the spinal region to receive therapy is useful to provide context for the present invention. As shown in FIG. 2A, a pre-sacral approach through percutaneous anterior track towards sacral target, through which trans-sacral axial bore will be made and channel extended distally for subsequent advancement of multi-level axial spinal stabilization assemblies. An anterior, pre-sacral, percutaneous tract extends through the "pre-sacral space" anterior to the sacrum. The pre-sacral, percutaneous tract is preferably used to introduce instrumentation to access and prepare (e.g., by drilling a bore in the distal/cephalad direction through one or more lumbar vertebral bodies and intervening discs). "Percutaneous" in this context simply means through the skin and to the posterior or anterior target point, as in transcutaneous or transdermal, without implying any particular procedure from other medical arts. However, percutaneous is distinct from a surgical access, and the percutaneous opening in the skin is preferably minimized so that it is less than 4 cm across, preferably less than 2 cm, and, in certain applications, less than 1 cm across. The percutaneous pathway is generally axially aligned with the bore extending from the respective anterior or posterior target point through at least one sacral vertebral body and one or more lumbar vertebral body in the cephalad direction as visualized by radiographic or fluoroscopic equipment. More specifically, as shown in FIG. 2b, the lumbar spine is accessed via a small skin puncture adjacent to the tip of the coccyx bone. The pre-sacral space is entered, using standard percutaneous technique, and the introducer assembly with the stylet's blunt tip serving as a dilator is placed through the paracoccygeal entry site. Once the tip of the stylet is through the facial layer, the blunt tip is rotated back against the anterior face of the sacrum and "walked" to the desired position on the sacrum under fluoroscopic guidance. Once the target site has been accessed and risk of soft tissue damage mitigated, the blunt-tipped stylet is removed and a guide pin, or wire, is safely introduced through the guide pin introducer tube, and "tapped in". The guide pin establishes the trajectory for placement of subsequent bone dilators and sheath through which a twist drill is introduced creating an axial bore track, the lumen of which is extended distally. The guide pin maintains the axial alignment of access & preparation tools as well as the alignment of cannulated spinal stabilization devices and assemblies, of larger diameter than the bore track, that are subsequently introduced over a 23" long, 0.090" diameter guide pin and through an exchange cannula for deployment of within the vertebral column, as described at least in part in co-pending and commonly assigned U.S. patent application Ser. Nos. 10/972,065; 10/971,779; 10/971,781; 10/971,731; 10/972,077; 10/971,765; 10/971,775; 10/972,299; and 10/971,780, all of which were filed on Oct. 22, 2004, and in co-pending and commonly assigned U.S. Provisional Patent Application 60/706,704, filed Aug. 9, 2005, and all of which are incorporated by reference herein in their entirety.

FIRST EXAMPLE

The present invention will now be described more fully hereinafter with reference to accompanying drawings in order to disclose selected illustrative embodiments. This invention may, however, be embodied in many different forms and should not be construed as limited to the embodiments set forth herein; rather these embodiments are provided so that the disclosure can be thorough and complete, and as part of the effort to convey the scope of the invention to those skilled in the art. Like numbers refer to like elements throughout.

Figure 3:
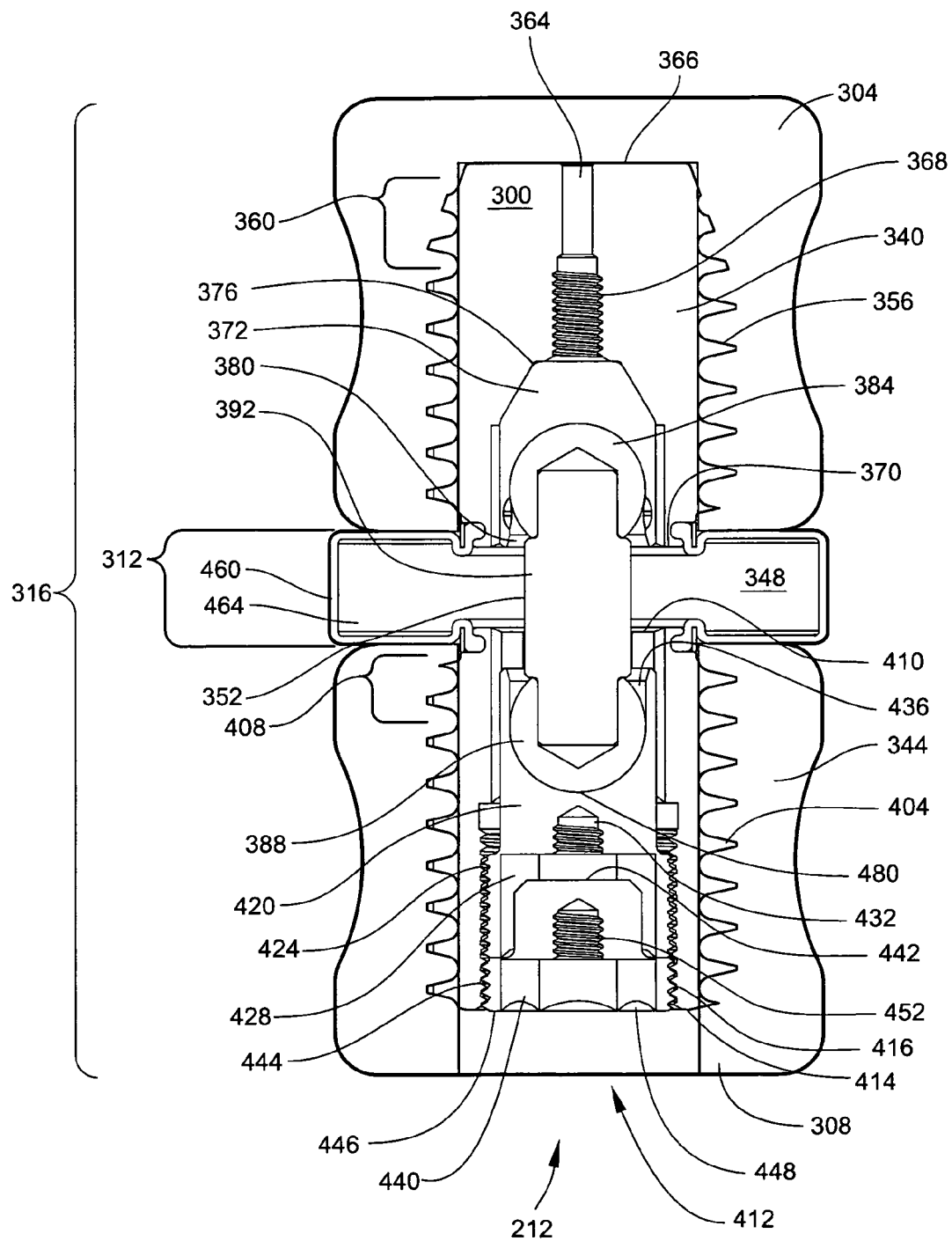
FIG. 3 illustrates an implanted motion preservation assembly 300 in a spinal motion segment.

In order to avoid the imprecision that can sometimes be introduced into a patent application while discussing many different alternative configurations at once, FIG. 3 starts with one very specific embodiment of the present invention. In order to provide an overview of the components and their placement with respect to a spinal motion segment, the explanation will start with an overview of an implanted device. Subsequent drawings will provide detail on the delivery and assembly of the device.

Figure 4:
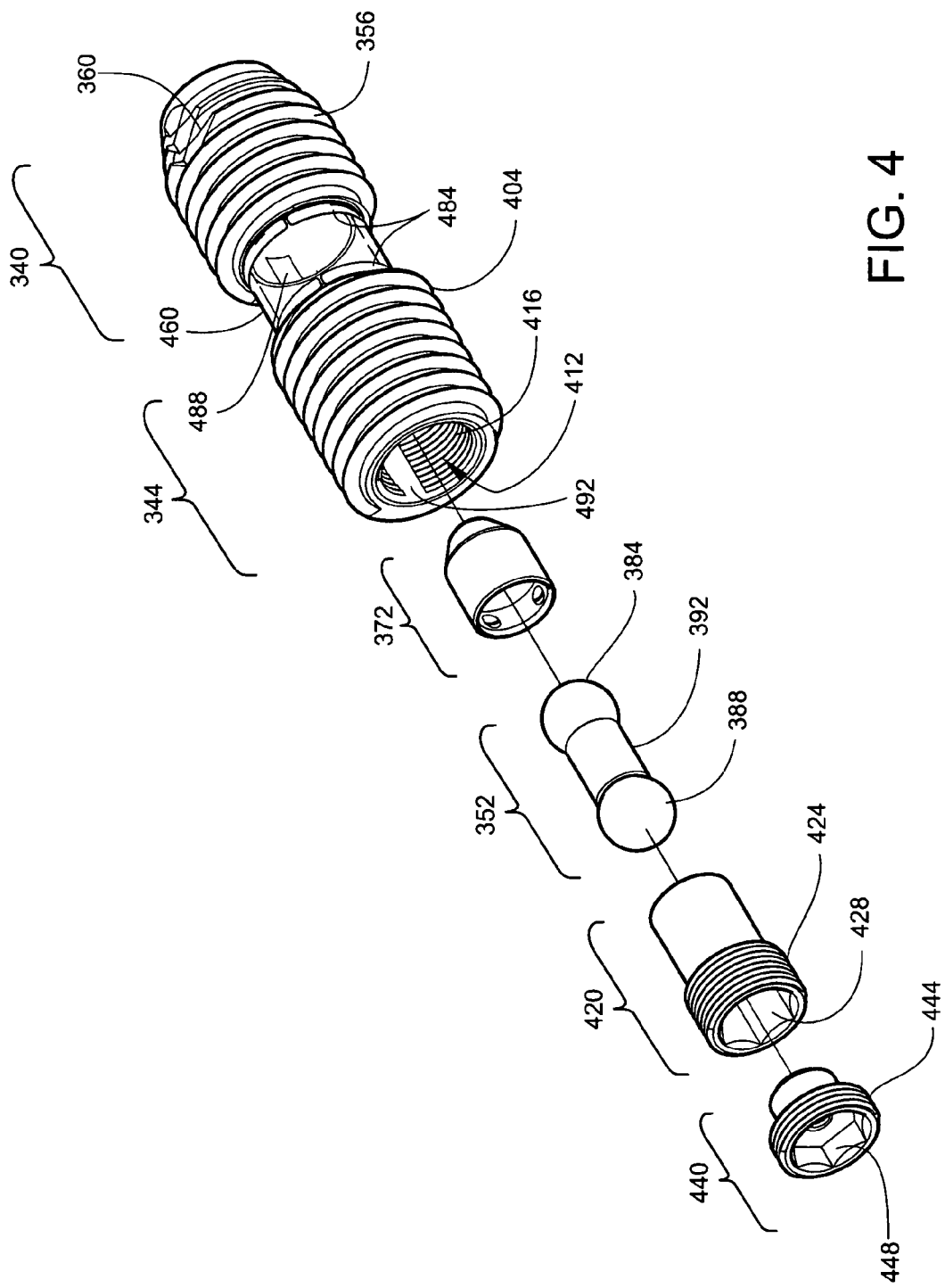
FIG. 4 is an exploded diagram that provides another view of the components described in FIG. 3.

FIG. 3 illustrates an implanted motion preservation assembly 300. FIG. 4 provides an exploded diagram that provides another view of the components described in FIG. 3.

Figure 1:
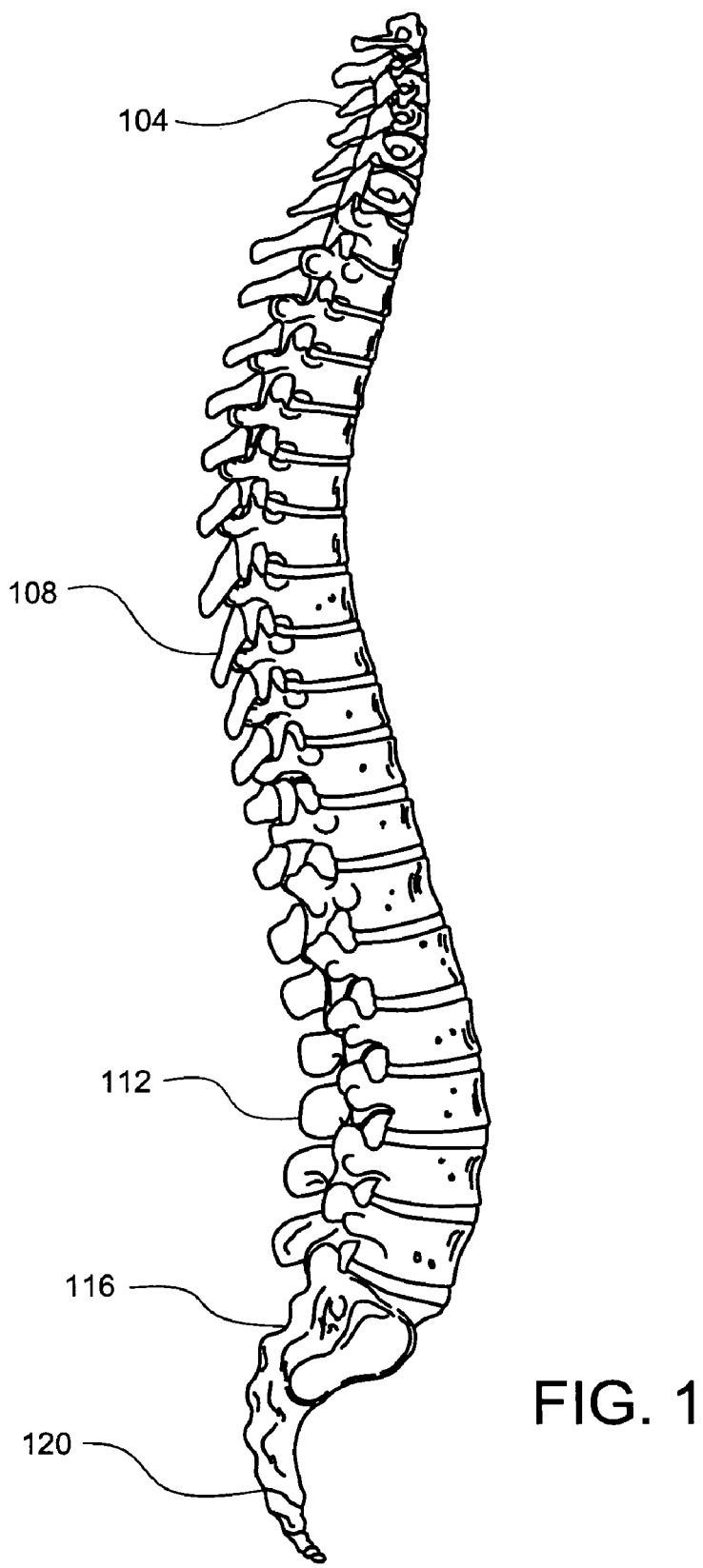
FIG. 1 identifies the sections of a human spine.

This motion preservation assembly 300 is implanted into a distal vertebral body 304 and a proximal vertebral body 308 and extends across an intervertebral disc space 312. The motion preservation assembly 300 would be placed in a previously prepared axial channel 212. Collectively, the distal vertebral body 304, the proximal vertebral body 308 and the intervertebral disc space 312 form a motion segment 316. The drawings of the vertebral bodies are not intended to convey anatomical details of the spinal components but to illustrate the placement of the assembled motion preservation assembly 300. One mapping of the components illustrated in FIG. 3 onto a spine would be for the distal vertebral body to be the L5 vertebral body 216 (See FIG. 2) at the caudal end of the lumbar section 112 (See FIG. 1) and the proximal vertebral body 308 would be the sacrum 116 (See FIG. 1). Alternatively, the motion segment could be more cephalad (and thus more distal to the surgeon) such as the L4/L5 vertebral bodies 220, 216 (See FIG. 2).

The major components of the motion preservation assembly 300 include the distal component (anchored in the superior, or distal vertebral body, herein also sometimes referred to as distal bone anchor) 340, proximal component (anchored in the inferior, or proximal vertebral body, herein also sometimes referred to as proximal bone anchor) 344, prosthetic nucleus 348 (generally including outer membrane 460), and a pivot 352.

Figure 5:
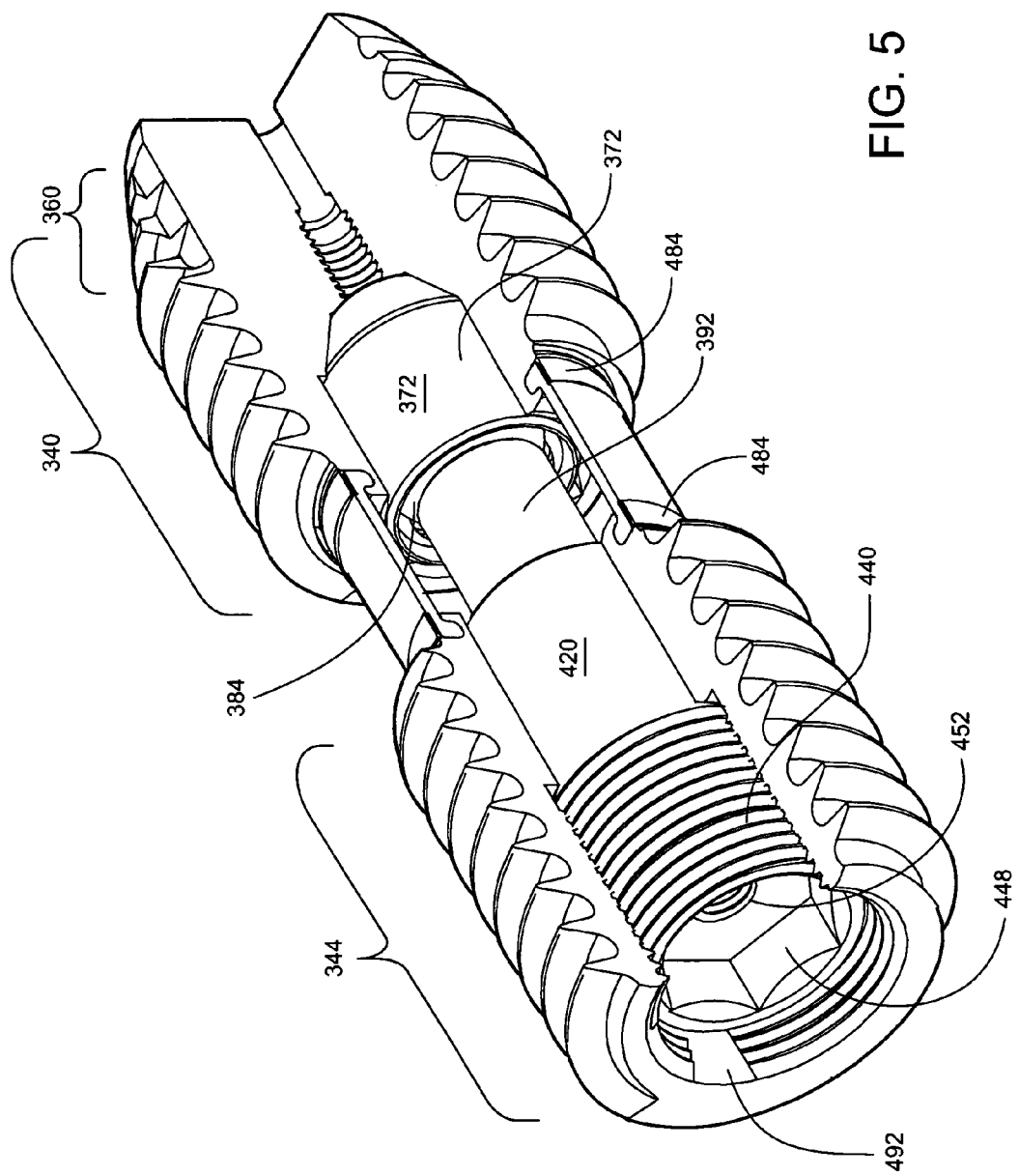
FIG. 5 provides a view of the motion preservation assembly in FIG. 3 with a quarter round section removed from the distal bone anchor 340 and the proximal bone anchor 344 to reveal the components within an assembled set of components.

The distal bone anchor 340 shown in FIG. 3 has a set of external threads 356. Advantageously, the set of external threads 356 can include a chip breaker section 360 at the distal end of the distal bone anchor to facilitate the starting of cutting a thread path into the distal vertebral body 304. The chip breaker section is best seen in FIG. 5. A chip breaker is a discontinuity in the thread that allows chips to break off as the thread path is cut. The axial channel 212 is created into the distal vertebral body 304, with the diameter of the axial channel 212 at the distal vertebral body 304 approximately equal to the minor diameter of the set of external threads 356.

The distal bone anchor 340 has a cavity 364 running from the distal face 366 of the distal bone anchor 340 to the proximal face 370 of the distal bone anchor 340. In this context, a face is the three dimensional surface of the part as viewed from that side, akin to the six three dimensional faces of die from a pair of dice. The cavity 364 is not of uniform cross section and serves several purposes. The distal end of the cavity 364 illustrates that the cavity can be used to allow the distal bone anchor 340 to be deployed over a guide wire. The cavity 364 includes an internal threaded section 368 which can be engaged by a driver, retention or extraction tool as described below. The cavity 364 in the distal bone anchor 340 shown in FIG. 3 contains a distal pivot cup 372 in a corresponding cup section 376 of the cavity 364.

The distal pivot cup 372 in turn has a cavity 380 which serves as a bearing surface for the distal end 384 of the pivot 352.

The pivot 352 shown in FIG. 3 has the distal end 384 referenced above and a proximal end 388 which in this embodiment are configured as substantially spherical components integral with the pivot body 392.

The proximal bone anchor 344 has a set of external threads 404 including a lead-in section 408. The proximal bone anchor 344 has a cavity 412 that runs from the distal face 410 of the proximal bone anchor 344 to the proximal face 414 of the proximal bone anchor 344. The cavity 412 is not uniform in cross section. A portion of the cavity 412 has a set of internal threads 416. Preferably, the pitch of the set of internal thread 416 will be relatively fine (perhaps 16 threads per inch up to 64 threads per inch). In the embodiment shown in FIG. 3, the proximal bone anchor cavity 412 contains a proximal pivot cup 420 that has a set of external threads 424 that engage with the set of internal threads 416 to allow torque from a driver (not shown) imparted to a driver engagement section 428 to rotate the proximal pivot cup 420 relative to the proximal bone anchor 344 to axially (distally) advance the proximal pivot cup 420. One can appreciate that axially advancing the proximal pivot cup 420 will cause the proximal pivot cup 420 to contact the pivot 352 and cause the pivot 352 to contact the distal pivot cup 372. After these components are in contact, further axial advancement of the proximal pivot cup 420 will cause the axial movement of the distal bone anchor 340 (and the distal vertebral body 304 engaged with the distal bone anchor 340) relative to the proximal bone anchor 344 (and the proximal vertebral body 308 engaged with the proximal bone anchor 344). This movement of one vertebral body away from another vertebral body causes a distraction of the intervertebral disc space between the two vertebral bodies.

Note that the distraction that can be achieved by rotation of the proximal pivot cup 420 is preferably used as an adjustment to alter the distribution of loading between the pivot and the prosthetic nucleus component of the motion preservation assembly. The primary means for achieving distraction is by means of the distraction and insertion tool 2032 in FIG. 20, as will be described below.

Returning to FIG. 3, the driver engagement section 428 could be configured among any one of many types of ways to impart torque with a driver. A female hex socket is a suitable choice. The proximal pivot cup 420 shown in FIG. 3 includes a threaded cavity 432 which can be engaged with a driver or extraction tool. The proximal pivot cup 420 includes a distal cavity 436 that serves as a bearing surface for the proximal end 388 of the pivot 352.

The cavity 412 in the proximal bone anchor 344 also includes a jam nut 440 with a distal end 442 and a proximal end 446. The jam nut 440 has set of external threads 444 adapted to engage with the set of internal threads. The jam nut 440 also has a driver engagement section 448 that is adapted to receive torque imparted by a corresponding driver such as a male hex driver. The torque input can cause the jam nut 440 to axially (distally) advance until it makes contact with the proximal pivot cup 420. The jam nut 440 shown in FIG. 3 also includes a threaded cavity 452 which can be used by a driver or extraction tool.

The prosthetic nucleus 348 includes an outer membrane 460 and prosthetic nucleus material 464. As outer membrane 460 is filled with prosthetic nucleus material 464, the outer membrane 460 expands to conformably contact the inferior endplate of the distal vertebral body 304, the superior endplate of the proximal vertebral body 308, and the inner wall of the annulus fibrosus (not shown) which collectively define the boundaries of an intervertebral disc space.

As FIG. 4 shows the various components before insertion into the body, the outer membrane 460 is shown before expansion with prosthetic nucleus material 464 to form a prosthetic nucleus 348 within the intervertebral disc space. FIG. 4 shows the pair of retainer rings 484 used as part of the mechanism to attach the outer membrane 460 to the distal bone anchor 340 and the proximal bone anchor 344 sufficiently to allow the membrane to be stretched to fill the intervertebral disc space without pulling away from the bone anchors. The attachment of the retainer rings 484 can be done in a number of ways including using adhesives, laser welding, crimping, or swaging. The ring could also be spring loaded or shrunk (e.g. nitinol or a heat shrink polymer). A preferred method of attachment uses the laser welding process to weld the circumference of the retainer rings 484 to the bone anchors 340 and 344, respectively. It is useful for the laser-welding process to compress the retainer ring 484 as it is being welded so that the ring is made smaller and thus more effective in holding the outer membrane 460 in place. Laser welding allows for the pinpoint application of energy so that welding occurs without transfer of large amounts of heat to the assembly which might adversely affect the membrane.

Figure 6:
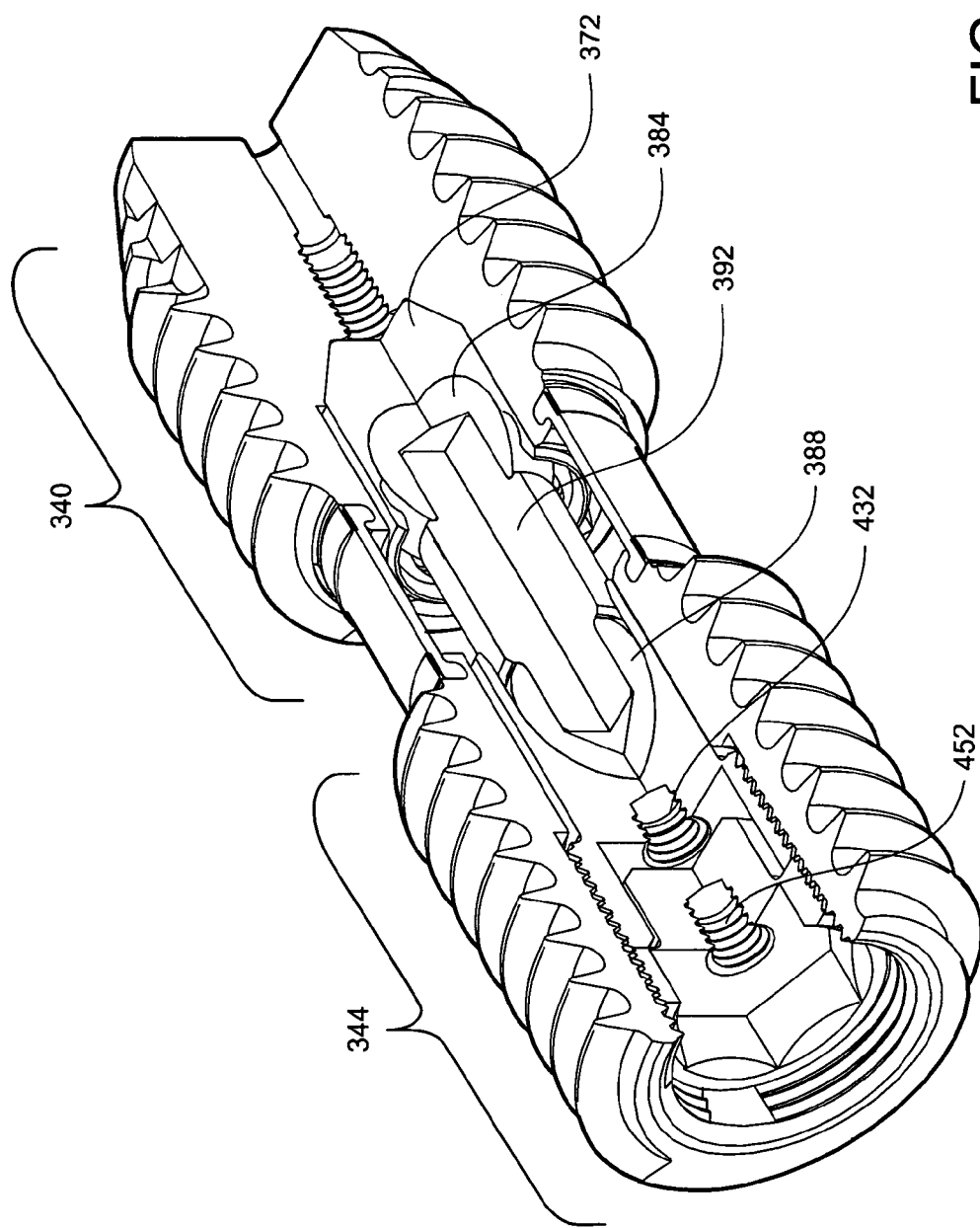
FIG. 6 is a view of the same motion preservation assembly 300 but with a quarter round of the entire assembly removed.

FIGS. 5 and 6 provide additional views of motion preservation assembly 300. FIG. 5 provides a view with a quarter round section removed from the distal bone anchor 340 and the proximal bone anchor 344 to reveal the components within an assembled set of components (but without the insertion of prosthetic nucleus material 464 as this device is not implanted in a motion segment). FIG. 6 is a view of the same motion preservation assembly 300 but with a quarter round of the entire assembly removed.

Figure 7:
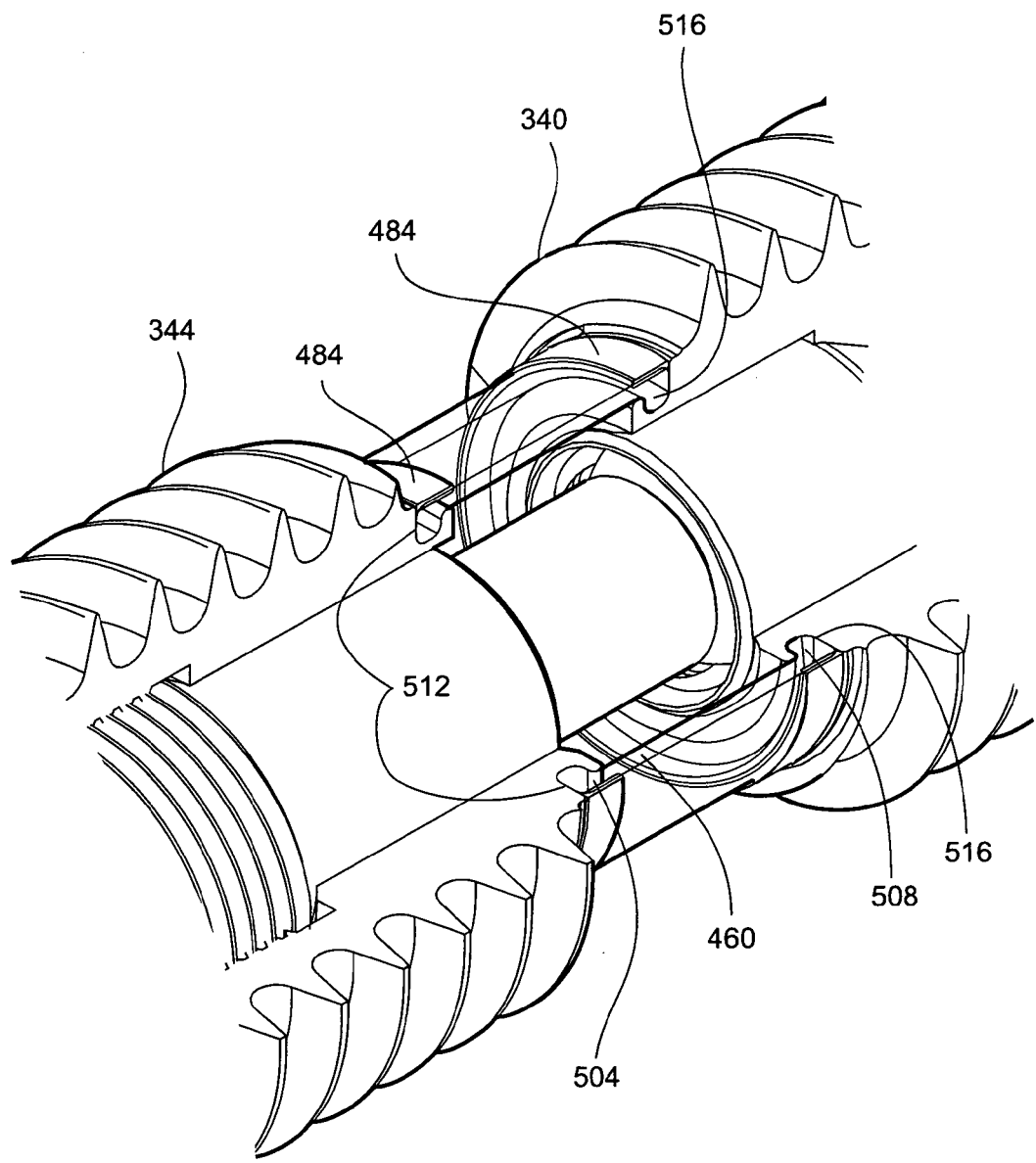
FIG. 7 shows an enlarged portion of FIG. 5.

FIG. 7 shows an enlarged portion of FIG. 5. FIG. 7 shows details of one method for connecting the outer membrane 460 to the distal bone anchor 340 and the proximal bone anchor 344. In a preferred embodiment, outer membrane 460 is configured as an expandable membrane, preferably comprised of an elastomeric material, e.g. silicone rubber, such as that obtained from Nusil Silicone Technology located in Carpeneria, Calif., exhibiting elongation of between about 500% and about 1500% and most preferably about 1000% and having a wall thickness of 0.220 inches. Outer membrane 460 has a distal end 508 which fits into a groove 516 on the proximal end of the distal bone anchor 340; and a proximal end 504 which fits into a groove 512 in the distal end of the proximal bone anchor 344. After retainer rings 484 are placed over the outer membrane ends 504 and 508, and along their respective circumferences to the bone anchors 340 and 344 (preferably while compressing the retainer rings 484 to make the ring smaller), the outer membrane 460 is firmly connected to the two bone anchors such that the outer membrane 460 will stretch significantly to fill the intervertebral disc space under pressure from inserted prosthetic nucleus material 464 without pulling free of either bone anchor 340 or 344.

Returning now to FIG. 3, it is preferred that the bulk prosthetic nucleus materials (PNM) (element 464 in FIG. 3) comprise elastomeric solids and/or viscoelastic gels, i.e., materials whose viscoelastic properties (e.g., rheology and compressibility) alone or in conjunction with the biomechanical properties of outer expandable membrane 460, enable them to perform in a functional manner which is substantially equivalent to the physiologic disc nucleus. Preferred prosthetic nucleus materials and systems comprise biomedical grade silicone elastomer e.g. silicone rubber, such as that obtained from Nusil Silicone Technology located in Carpeneria, Calif. or hydrogels or blends thereof (e.g., hydrogel/hydrogel, or hydrogel/elastomer). Cross-linked hyaluronic acid, such as is available from Fidia Corporation in Italy, is an example of a suitable material, however, many natural and man-made hydrogels or blends thereof may be configured to achieve similar properties without inflammatory response, such as those disclosed and described in co-pending and commonly assigned United States Patent Applications referenced above, and in detail in particular in U.S. Provisional Patent Application 60/599,989 filed Aug. 9, 2004, and 60/558,069 filed Mar. 31, 2004, each of which are incorporated in their entirety into this disclosure by reference. Priority is also claimed to co-pending and commonly assigned U.S. patent application Ser. No. 11/199,541 filed Aug. 8, 2005 for "Prosthetic Nucleus Apparatus and Methods" and the provisional 60/599,989 filed Aug. 9, 2004 claimed as a priority document in the '541 application. Both of these applications are incorporated in their entirety into this disclosure by reference.

Timed Delivery FIG. 4 provides a view of slot 488 in the cavity (364?) of the distal bone anchor 340 and the slot 492 in the cavity 412 of the proximal bone anchor 344. The use of these two slots allows for a keyed delivery of the two components. A keyed (or timed) delivery of the two bone anchors 340 and 344 allows for control over the rotational position of the two sets of threads. The purpose of this controlled delivery is to avoid cross threading. More specifically, when electing to use the same thread pitch for the external threads 356 on the distal bone anchor 340 and on the external threads 404 on the proximal bone anchor 344, the distal bone anchor 340 can be made with as large a cross section (rod diameter) as the proximal bone anchor 344. Having a large cross section is desirable as it makes it easier to design a distal bone anchor with adequate strength and maximum engagement between the threads and the bone of the distal vertebral body.

If the minor diameters and the major diameters of the threaded portions of distal bone anchor 340 and the proximal bone anchor 344 are the same, then the bores through the proximal vertebral body 308 and the distal vertebral body 304 created during the process of creating the axial channel 212 would be the same size. As the distal bone anchor 340 is moved towards the bore in the distal vertebral body 304, the distal bone anchor 340 is first axially advanced by rotating it through the bore in the proximal vertebral body 308. As the distal bone anchor 304 is rotatably advanced through the proximal vertebral body 308, the external threads 356 cut a helical thread path into the bone around the bore in the proximal vertebral body 308 as the bore is approximately the size of the minor diameter of the external threads 356 and the major diameter of the external threads 356 extends beyond the bore into the bone. Without timing or keyed delivery, the subsequent axial advancement of the proximal bone anchor 344 would tend to cut a new helix into the bone around the bore in the proximal vertebral body 308. This second helix would meet added resistance as the bone has just received a newly cut thread helix, and the strength of the connection between the external threads 404 on the proximal bone anchor 344 is compromised by previously cut and now unused thread path through the bone. In contrast, timed delivery allows the leading edge of the helical thread on the exterior of the proximal bone anchor 344 to enter into the helical thread path left by the external threads 356 on the distal bone anchor 340. An alternative to timed delivery is to size the major diameter of the external threads on the distal bone anchor to be less than the diameter of the bore in the proximal vertebral body and then prepare a bore in the distal vertebral body that is approximately the size of the minor diameter of the external threads on the distal bone anchor.

Distraction of the Motion Segment though use of Dissimilar Thread Pitches

Previously filed applications assigned to Trans1, Inc. have described a process for imposing a distraction on a motion segment (to move the two vertebral bodies away from each other along the z axis). For example see U.S. Pat. No. 6,921,403 for Method and Apparatus for Spinal Distraction and Fusion. Thus, when a threaded rod with a distal threaded section of a first, finer thread pitch engages with a distal vertebral body (after passing through a bore in the proximal vertebral body larger than the major diameter of the threads on the distal threaded section) and a proximal, coarser threaded section on the same threaded rod engages with a proximal vertebral body, the rotation of the two threaded sections with different thread pitches causes the distal finer pitched threads to advance into the distal vertebral body slower than the coarser threads advance into the proximal vertebral body. The net effect is that the engagement of the two threaded sections with the two vertebral bodies causes the two vertebral bodies to move apart.

This same method could be used to impose an axial distraction when using bone anchors for the present invention if the bone anchors are placed on a single driver that can maintain a predetermined spatial separation between non-contiguous bone anchors and impose the same rotation on each bone anchor. A driver of this type is described in co-pending provisional application co-pending and commonly assigned U.S. Provisional Application No. 60/621,730 filed Oct. 25, 2005 for "Multi-Part Assembly for Introducing Axial Implants into the Spine" which is incorporated by reference.

Alternative Means for Imposing a Distraction

While distraction could be imposed using dissimilar thread pitch as described above, an alternative and preferred means of distraction is used with a tool discussed below in connection with FIG. 20 that pushes on the distal pivot cup as the tool is axially advanced by engagement with internal threads in the proximal bone anchor.

Degrees of Freedom and Limitations

As FIGS. 3 through 7 are static and the desired attributes of a motion preservation assembly are dynamic stabilization, it is appropriate to dwell on how the motion segment can move with an implanted motion preservation device.

If one looks at pivot point 480 located just above the threaded cavity 432 in the proximal pivot cup, one can start to count the ways that the distal bone anchor 340 and corresponding distal vertebral body 304 can move relative to the pivot point 480. The first type of movement is axial rotation (clockwise or counterclockwise). Nothing in this particular motion preservation device places a limit on the amount of clockwise or counterclockwise motion. As discussed above a system that allows about two degrees of rotation on this axis would support the normal range of motion on this axis. (Note: range and degree of motion will vary according to vertebral level—e.g., L4-L5 not same as L5-S1)

As the normal full range of motion typically allows for about 12 degrees of flexion, about 8 degrees of extension, about 9 degrees of left or right lateral bend, in order to avoid constraining the normal range of motion an installed motion preservation device would need to allow at least these amounts of rotation. The precise range and degree of motion for a motion segment varies along the motion segments of the spine. For example the range and degree of motion in the L4-L5 motion segment will not be exactly the same as for the L5-S1 motion segment.

The device shown in FIG. 3 is radially symmetric around the z axis so it does not need to be positioned in a particular orientation in order to provide the maximum capacity for rotation in a particular direction (for example flexion versus extension or lateral bending). The rotation of the implanted distal bone anchor with respect to the proximal bone anchor can be achieved through a combination of the action of the proximal pivot head 388 moving with respect to the proximal pivot cup 420 and the action of the distal pivot head 384 with respect to the distal pivot cup 372.

Figure 8A:
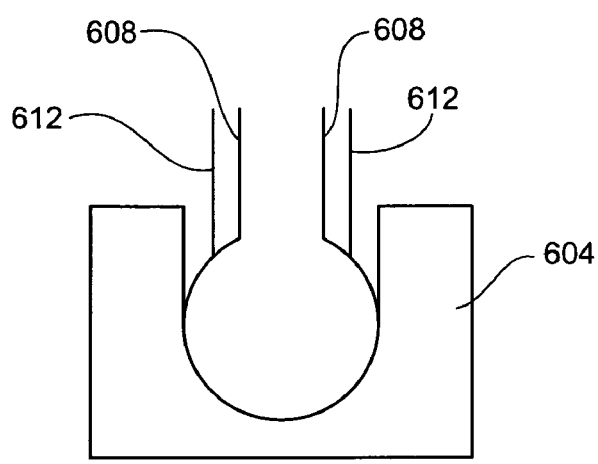
FIG. 8A illustrates the effect of using two different pivot body widths.
Figure 8A:
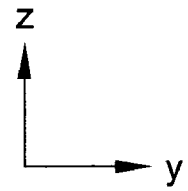
Figure 8B:
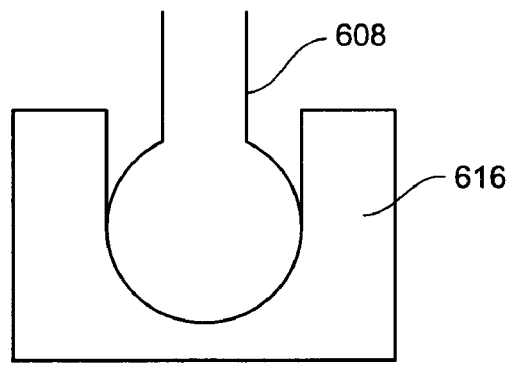
FIG. 8B illustrates the effect of changing the depth of the pivot end cup.
Figure 8B:
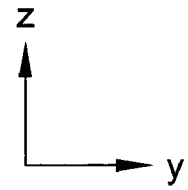

One can change the maximum pivot angle of a pivot with respect to the corresponding pivot cup by varying two parameters, the depth of the cavity in the pivot cup and the width of the pivot body with respect to the pivot cavity. FIG. 8A and FIG. 8B illustrate these concepts. FIG. 8A illustrates two different pivot body widths. If a pivot body was changed from width 608 to width 612, then the wider pivot body 612 would hit the pivot end cup 604 after a smaller amount of rotation than if the pivot body remained with width 608.

FIG. 8B uses the pivot body of FIG. 8a but places it in a pivot end cup 616 that is not as deep so that the pivot can rotate with respect to the pivot end cup more in FIG. 8B than in FIG. 8A.

The use of two pivots allows for translation of one implanted bone anchor relative to the other in the x-axis (anterior/posterior), y-axis (lateral) or a combination of the two. In order to appreciate the advantage of using two pivots, it is useful to look at the movement when there is one pivot. In FIG. 9A, a single pivot 650 is engaged with a bearing surface in proximal bone anchor 654 and fixed to distal bone anchor 658. When the pivot 650 rotates in the x-z plane away from the z axis as shown in FIG. 9B, the distal bone anchor 658 moves in rotation with respect to the proximal bone anchor 654 to change the relative orientation of the one bone anchor to the other.

Figure 9:
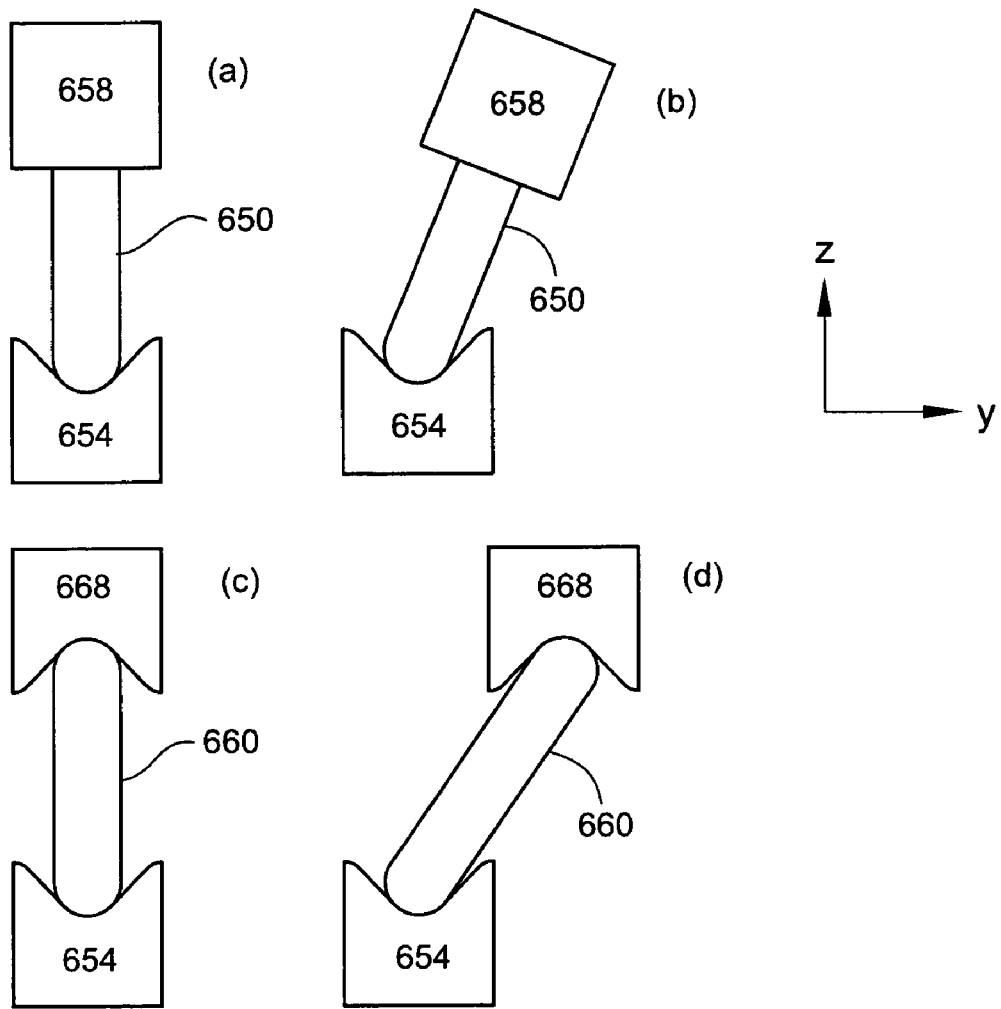
FIG. 9 illustrates the advantage of a dual pivot over a single pivot.

In contrast, in FIG. 9C, the pivot 660 is a dual pivot and thus can pivot with respect to proximal bone anchor 654 or distal_bone anchor 668. Now the distal bone anchor 668 can move in substantially pure translation along the x axis with respect to the proximal bone anchor 654. The relative orientations of the bone anchors are preserved as the movement did not impose a rotation on the distal bone anchor 668. The term substantially pure translation was used as the elevation of the distal bone anchor 668 changed slightly during the movement from the state shown in FIG. 9C to the state shown in FIG. 9D which would not happen in pure x axis translation. While this example showed translation in the x axis, the same type of movement as shown in FIG. 9 would happen in the y axis or in a mix of x and y components unless the pivots were restrained in some way.

The example shown in FIG. 3, does not provide significant capacity for significant additional x or y translation as the pivot cups are substantially the same size as the pivot ends placed in the pivot cups. Expanding the pivot cups to exceed the maximum diameter of the pivot end sphere by 5 millimeters will provide some additional capacity for translation. Doing this in both pivot cups will add a second additional amount of possible translation.

Figure 10:
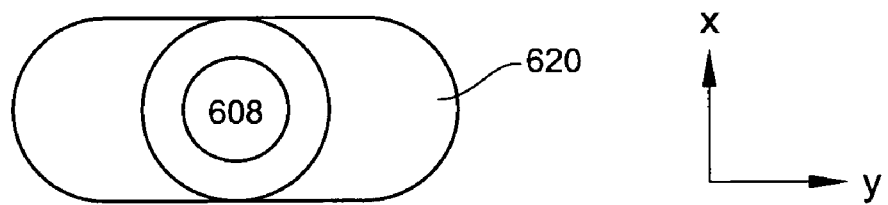
FIG. 10 illustrates a non-symmetric cavity in the pivot cup to allow for a greater amount of additional allowed translation in one direction as compared with another direction.

The example shown in FIG. 3 uses radially symmetric pivot ends and pivot cup cavities. Using a non-symmetric cavity in the pivot cup could allow for a greater amount of additional allowed translation in one direction as compared with another direction. FIG. 10 shows an example of this concept. Looking down on half a pivot 608, the wall of the pivot body and the maximum dimension of the spherical head of the pivot are both shown. Also shown is raceway 620 which serves as the constrained area for the pivot 608 to move within. Note that additional translation in the x direction is extremely limited but a much greater amount of additional translation is in the y (lateral) direction. When using such an asymmetric raceway, the insertion technique would need to control the orientation of the bone anchor so that the elongated direction of the raceway was aligned in the proper direction. One method is to insert the components in a particular orientation with respect to the driver. The driver would have a marker on it so that the driver marker could be monitored to ensure placement of the components in proper orientation with the anterior/posterior and lateral axes. Orientation of pivot cups within inserted bore anchors could be controlled by having a key and slot engagement between the pivot cup and bore anchor.

Figure 11:
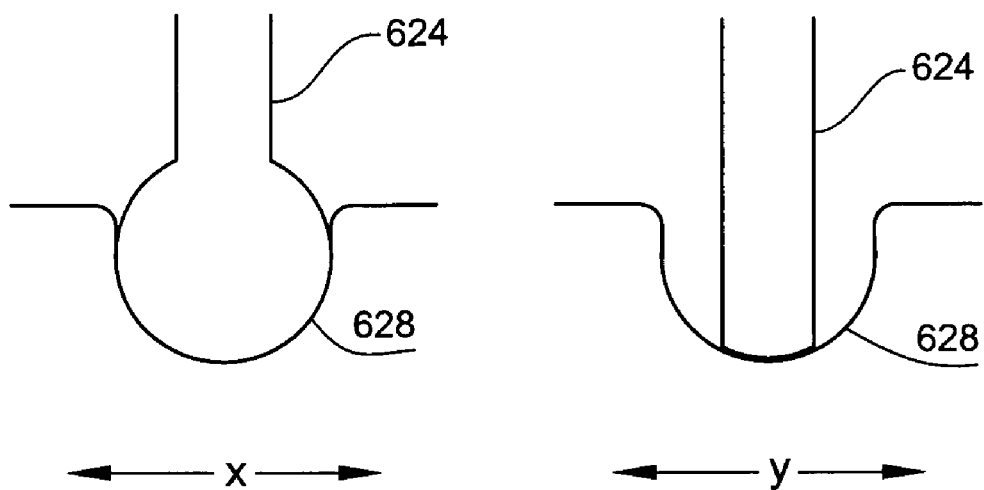
FIG. 11 illustrates an asymmetric pivot.

A way to allow more bending in one direction than in the other is to have an asymmetric pivot. FIG. 11 illustrates an asymmetric pivot 624 (only one end of the pivot is shown) in a pivot cup 628. This asymmetric pivot provides more limitation on the movement in the x direction (anterior/posterior) than in the y direction (lateral left/lateral right). When using an asymmetric component, it is important that the installation procedure place the asymmetric component in the proper starting position. Note, that although the device supports unlimited rotation along the z axis, the positioning of the asymmetric pivot will remain relatively constant as the range of axial rotation for an individual motion segment is only approximately two degrees clockwise and approximately two degrees counterclockwise.

In order to provide the 6$^{th}$ degree of freedom, translation in the z axis, the motion preservation assembly would need to allow the distal bone anchor to move in the z axis relative to the proximal bone anchor. (A careful observer will note that the translation in the x or y axis achieved through the use of dual pivot points will incidentally provide for a change in the z axis but a force purely along the z-axis would not cause this sort of translation.) Adding a degree of freedom for z-translation can be achieved in theory by a device that elongates in tension. However, tensile loads that impart a distraction on a motion segment are rare. The most common being the therapeutic application of traction to extend the spine.

Thus, the more useful capacity for translation in the z-axis is the ability to compress. Ideally, the compression would be reversible and repeatable. Thus, the deformation from the compression would need to be elastic. Elasticity is the property whereby a solid material changes its shape and size under force but recovers its original configuration when the forces are removed. For many people, elastic deformation brings to mind a rubber ball that can be deformed and then resumes its original shape. Bladders can undergo elastic deformation (examples include pneumatic tires and the bladders in soccer balls). Elastic deformation can be achieved through use of springs including disc springs of various types such as a Belleville disc spring or comparable spring.

Addition of an elastically deformable component in the motion preservation assembly would allow this motion segment to contribute to the spinal columns ability to compress under a heavy compressive force such as landing on feet after jumping or falling onto the buttocks. As the set of motion segments are in a stack, the lack of ability of one motion segment to elastically compress is tolerable as it is tolerated for the people who have a fused motion segment. Having some ability to elastically compress in the z direction is thought to be desirable especially for motion preservation devices with prosthetic nuclei as these ideally mimic the behavior of a natural motion segment.

Elastic deformation of the motion preservation device to allow the endplates of the distal vertebral body and the proximal vertebral body to move closer together would apply a compressive force on the prosthetic nucleus that assumed a conforming fit shape that contacts the endplates of these vertebral bodies. Compression of the prosthetic nucleus in the z direction causes it to expand radially outward to maintain the overall volume of the prosthetic nucleus. As the prosthetic nucleus expands radially outward, it transfers forces to the various layers of the annulus fibrosus, thus mimicking the natural transfer and dissipation of physiologic loads.

Having a motion preservation device with the ability to undergo elastic deformation in the z axis and the ability to promote radial distribution of loads to the annulus fibrosus to mimic normal physiological load sharing is apt to reduce the risk of subsidence or transition syndrome.

Introduction of Elastically Deformable Components.

One option for the use of an elastically deformable component in order to aid the ability for compressive axial translation and load distribution is to place an O-ring, elastomeric washer, or other elastomeric object between the distal end of the distal pivot cup 372 and the distal bone anchor 340. Ideally, the distal pivot cup or the distal bone anchor, or both would be shaped to allow space for the elastomeric material. Such elastomeric components may be configured from semi-compliant materials, for example fluoropolymer elastomer (Viton™), polyurethane elastomer, or silicone rubber.

Another location that could be used for the placement of an elastomeric component is within the proximal bone anchor between the proximal pivot cup and the jam nut. (embodiment not shown). In this configuration the proximal pivot cup would not have external threads so that it would be free to move axially in the cavity of the proximal bone anchor to compress the elastomeric material between the proximal end of the proximal pivot cup and the distal face of the jam nut. Yet another location for placement of the elastomeric surface is between the bearing surface and the pivot.

Figure 12:
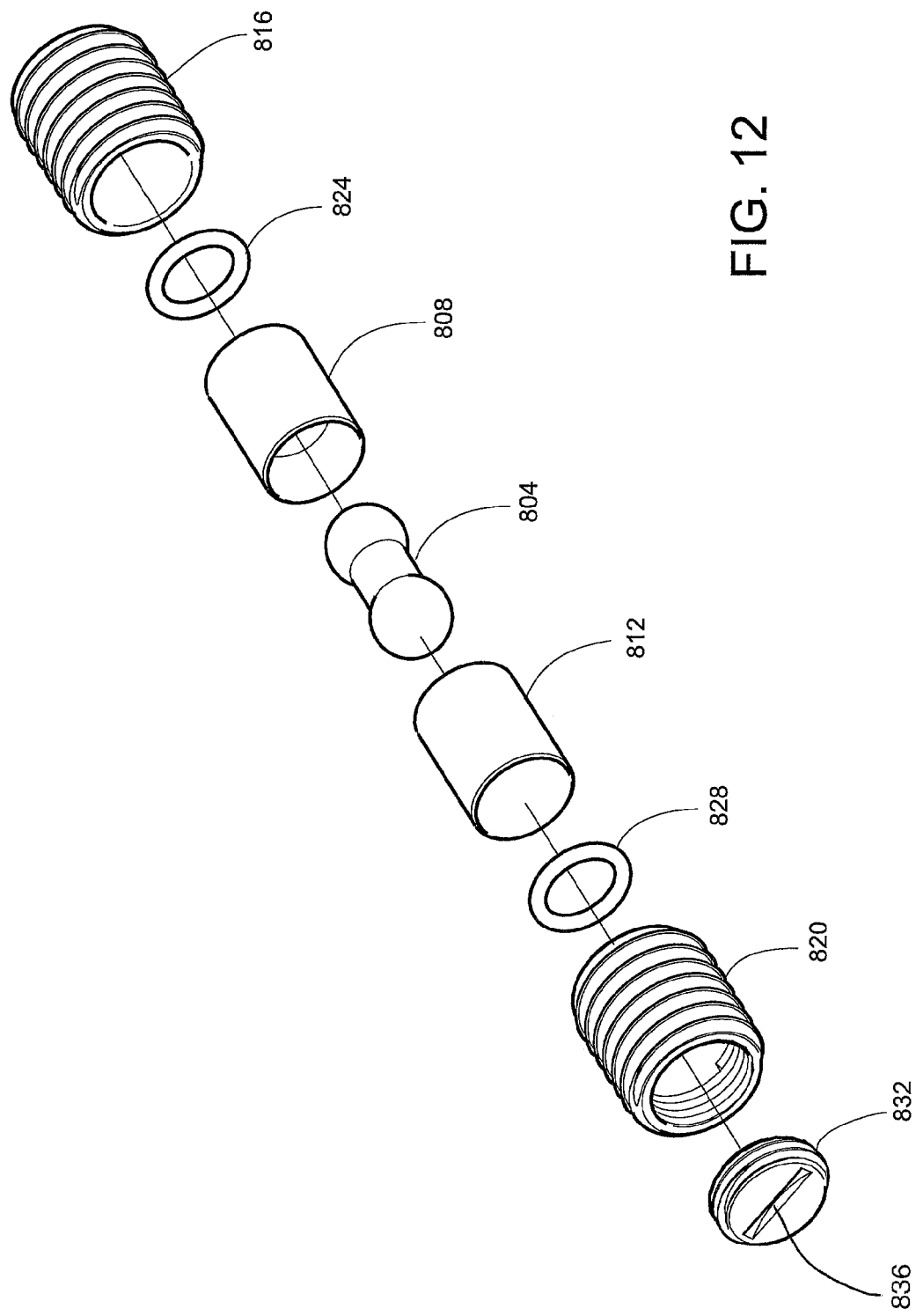
FIG. 12 illustrates one motion preservation assembly with elastomeric components.

FIG. 12 illustrates one motion preservation assembly 800 with elastomeric components. More specifically, motion preservation assembly 800 has a pivot 804 which fits into a cavity in a distal pivot cup 808, the cavity providing a bearing surface for the distal end of the pivot 804. The other end of the pivot 804 fits inside a cavity in a proximal pivot cup 812 which again provides a bearing surface. The exteriors of the distal pivot cup 808 and the proximal pivot cup 812 are not threaded and the pivot cups can move longitudinally within cavities in a distal bone anchor 816 and a proximal bone anchor 820. A distal O-ring 824 is placed between the distal pivot cup 808 and the cavity wall in the distal bone anchor 816. Likewise, a proximal O-ring 828 is placed between the proximal pivot cup 812 and the threaded cap 832 which engages a set of internal threads on the proximal end of the cavity in the proximal bone anchor 820. The threaded cap 832 has a slot 836 for receipt of a similarly shaped driver to impart torque to the threaded cap. With sufficient input to the slot 836, the threaded cap can be used to impart a distraction on the motion segment with this motion preservation device inserted by axially (distally) advancing the threaded cap 832, the O-ring 828 (which also compresses), the proximal pivot cup 812, the pivot 804, the distal pivot cup 808, the distal O-ring 824 and the distal bone anchor 816. As the axial movement of the threaded cap 832 was relative to the proximal bone anchor 820, the movement of all the other components causes the movement of the vertebral body engaged with the distal bone anchor 816 to move relative to the vertebral body engaged with the proximal bone anchor 820.

One of skill in the art will recognize that the use of a single O-ring is a viable alternative to using two O-rings. One of skill in the art will recognize that when using two elastomeric inserts in a single motion preservation assembly, the elastomeric inserts could have different properties such as being made of different thicknesses or from different elastomeric materials so that one responded under lower axial loads than the other.

Given an appropriate modification to the shapes of the components within the motion preservation assembly, the O-rings could be replaced with other elastomeric components such as washer shaped components. The O-rings could also be replaced with springs of various configurations and stiffness that would allow for elastic deformation without reliance on the use of elastomeric components.

A coil spring is one option. Another option is one of the various types of spring washer products such as a Belleville disc. Spring washers can be stacked to provide for greater total deflection or simply to change the response curve of deflection to force.

Machined Springs

Figure 13:
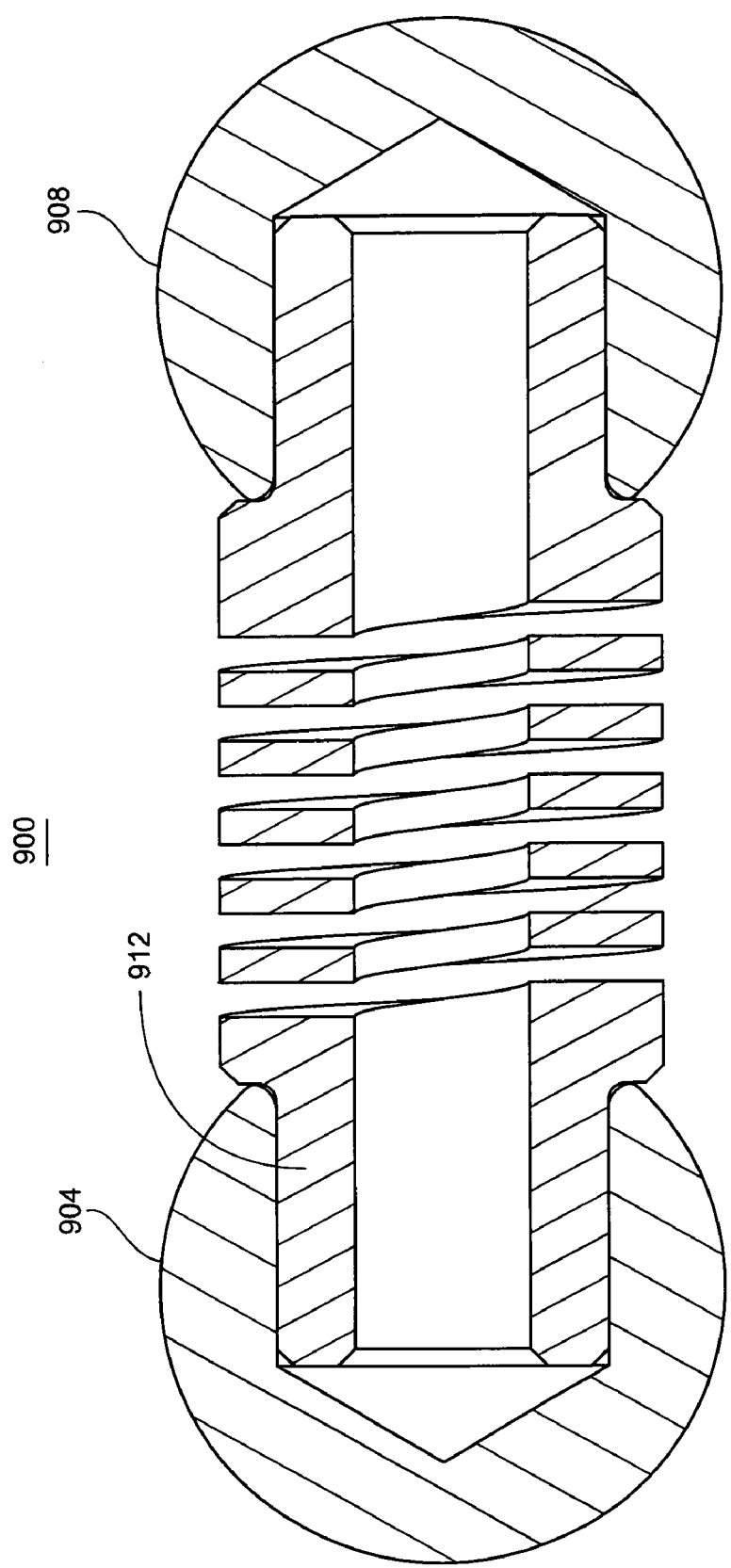
FIG. 13 illustrates a cross section of a pivot 900 with a machined spring connecting the two ends.

FIG. 13 illustrates a cross section of a pivot 900 with a first end 904, a second end 908, and a machined hollow rod 912 connecting the two ends. Springs machined into hollow rods (as opposed to springs created from coil stock) can be made with great precision which decreases the variation between machined springs.

Another use of machined springs is in pivot cups without external threads such as the pivot cups shown in FIG. 12. Pivot cups with integrated machined springs would have a first section that receives one end of the pivot and serves as the bearing surface. The remainder of the pivot cup could include a cylindrical portion which could be machined to incorporate a machined spring.

Alternative Embodiments

Figure 14:
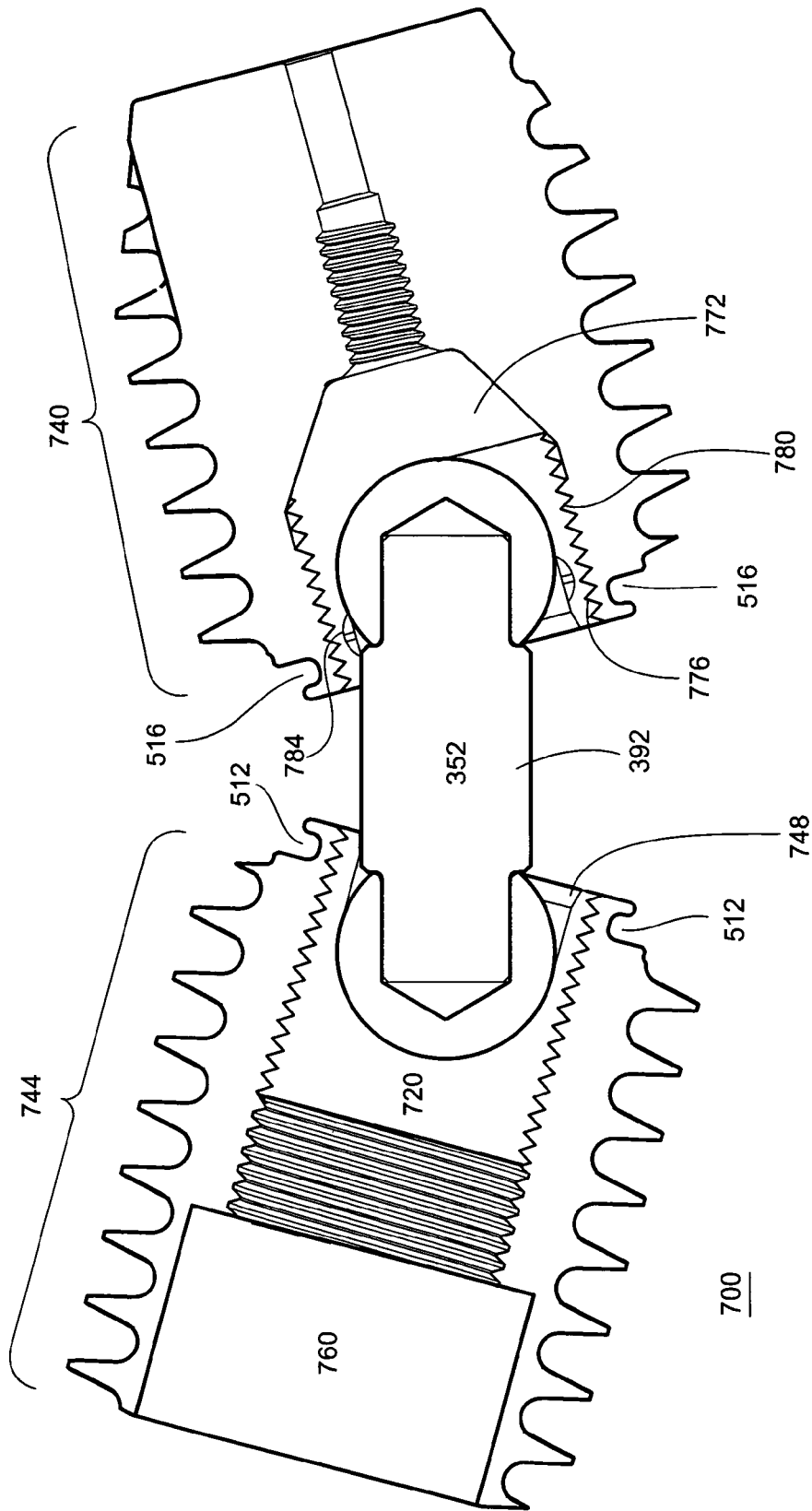
FIG. 14 illustrates an alternative embodiment of the motion preservation assembly with a externally threaded distal pivot cup.

FIG. 14 illustrates an alternative embodiment of the motion preservation assembly 300 discussed above. Distal bone anchor 740 and proximal bone anchor 744 are shown with a pivot 352 but without outer membrane 460 (see FIG. 7). The groove 512 in the distal end of the proximal bone anchor and the groove 516 in the proximal end of the distal bone anchor are visible in this figure. The principal differences between this motion preservation assembly 700 and the motion preservation assembly 300 is that the distal pivot cup 772 has external threads 776 and is threaded into a corresponding set of internal threads 780 in the cavity of the distal bone anchor 740, and that prosthetic nucleus material 464 is introduced directly into the intervertebral disc space, instead of filling the outer membrane, either with or without an accompanying sealant step of the surfaces of the intervertebral disc space by means of materials and methods such as described in co-pending and commonly assigned U.S. patent application Ser. No. 11/199,541 filed Aug. 8, 2005, and further described briefly below. Note that the distal pivot cup 772 has detent concavities 784 which can be engaged by a detent protrusion of a corresponding driver to impart torque to the distal pivot cup 772 to rotate it into threaded engagement with the distal bone anchor 740.

FIG. 14 illustrates the use of a cavity bevel 748 along the leading edge of the cavity that receives an end of the pivot 352 as the cavity bevel 748 allows the pivot body 392 to travel further before contacting the cavity wall. In this context, "travel further" is further than would be possible with the same components except that the cavity wall did not include a bevel.

FIG. 14 shows a proximal pivot cup 720 (shown in cross-section to allow viewing of the pivot) that engages with the threaded interior of the proximal bone anchor 744 and a jam nut 760.

Figure 15:
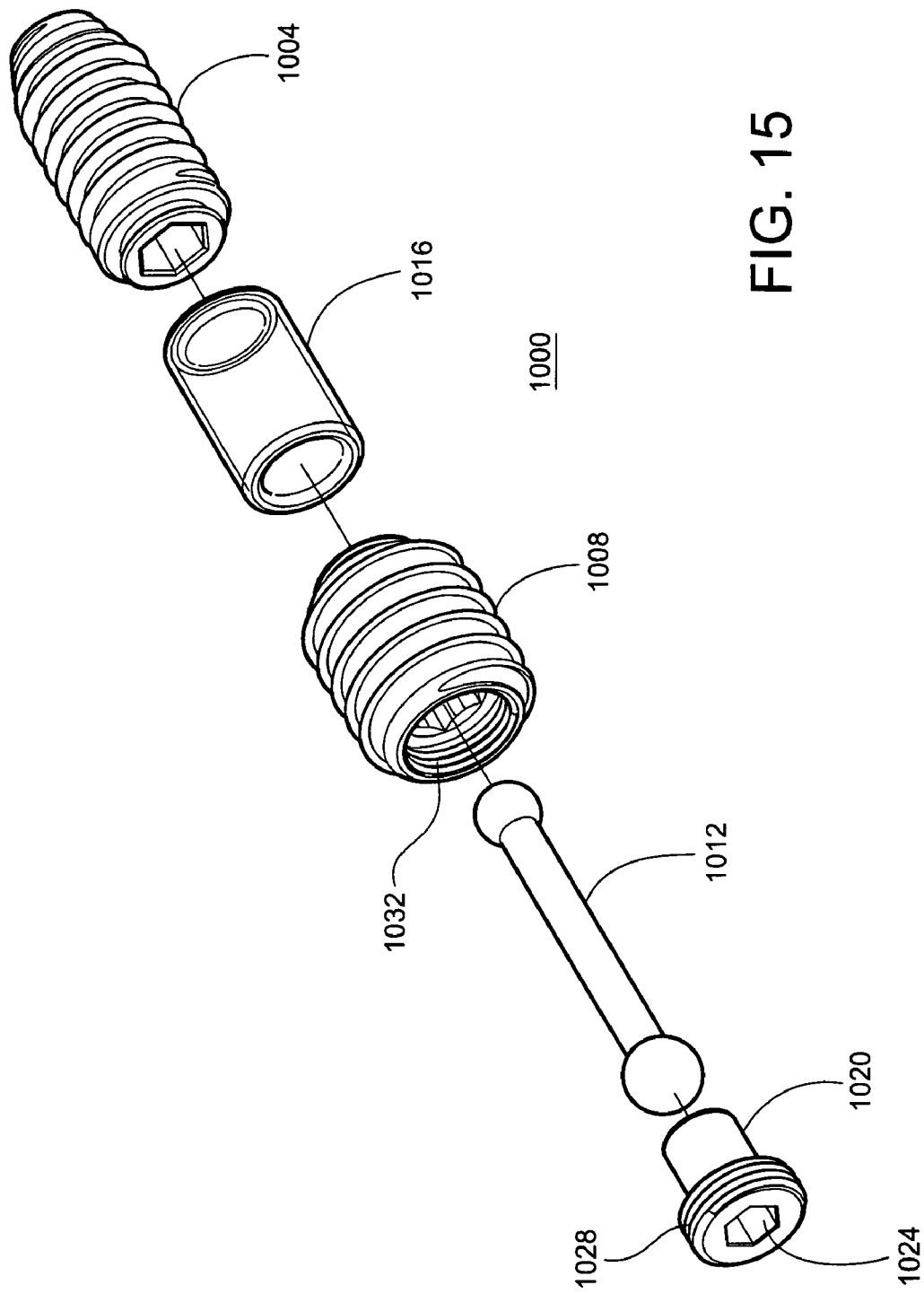
FIG. 15 shows an exploded view of another motion preservation assembly distal implanted component having an integrated bearing surface.

FIG. 15 shows an exploded view of another motion preservation assembly 1000. This motion preservation assembly 1000 differs from motion preservation assembly 300 in several respects. Motion preservation assembly 1000 has a distal bone anchor 1004 with an integrated bearing surface (not visible). The motion preservation assembly 1000 has a proximal bone anchor 1008 with a cavity that runs through the proximal bone anchor. A pivot 1012 can be inserted through the proximal bone anchor 1008 and a membrane 1016 connected to the proximal bone anchor 1008 and the distal bone anchor 1004. Pivot 1012 is illustrative of the more general point that the length of the pivot body can be different from pivot to pivot and this variation can be used to create a combination of components tailored to the anatomy of a specific patient.

The distal end of the inserted pivot 1012 makes contact with the bearing surface of the distal bone anchor 1004. A threaded cup 1020 with integrated bearing surface (not visible) has a driver engagement section 1024 which can be torqued by a corresponding driver to rotate and axially advance the threaded cup 1020 within the proximal end of the cavity in the proximal bone anchor through engagement between a set of external threads 1028 on the threaded cup and a set of internal threads 1032 in the cavity of the proximal bone anchor 1008.

It is considered preferable to have a bearing surface without a cavity interrupting the continuity of the bearing surface. Thus, when a distal bone anchor is to have an integrated bearing surface for engagement with the pivot, the deployment means should preferably not use a guide wire. Likewise, it would be preferable to not use a threaded cavity, such as element 368 in FIG. 3, as that would lead to a discontinuity or gap in the bearing surface.

These preferences for having a continuous bottom for the bearing surface without additional cavities can be supported as other methods exist for deploying a distal bone anchor including the use of detents and detent concavities.

Figure 16:
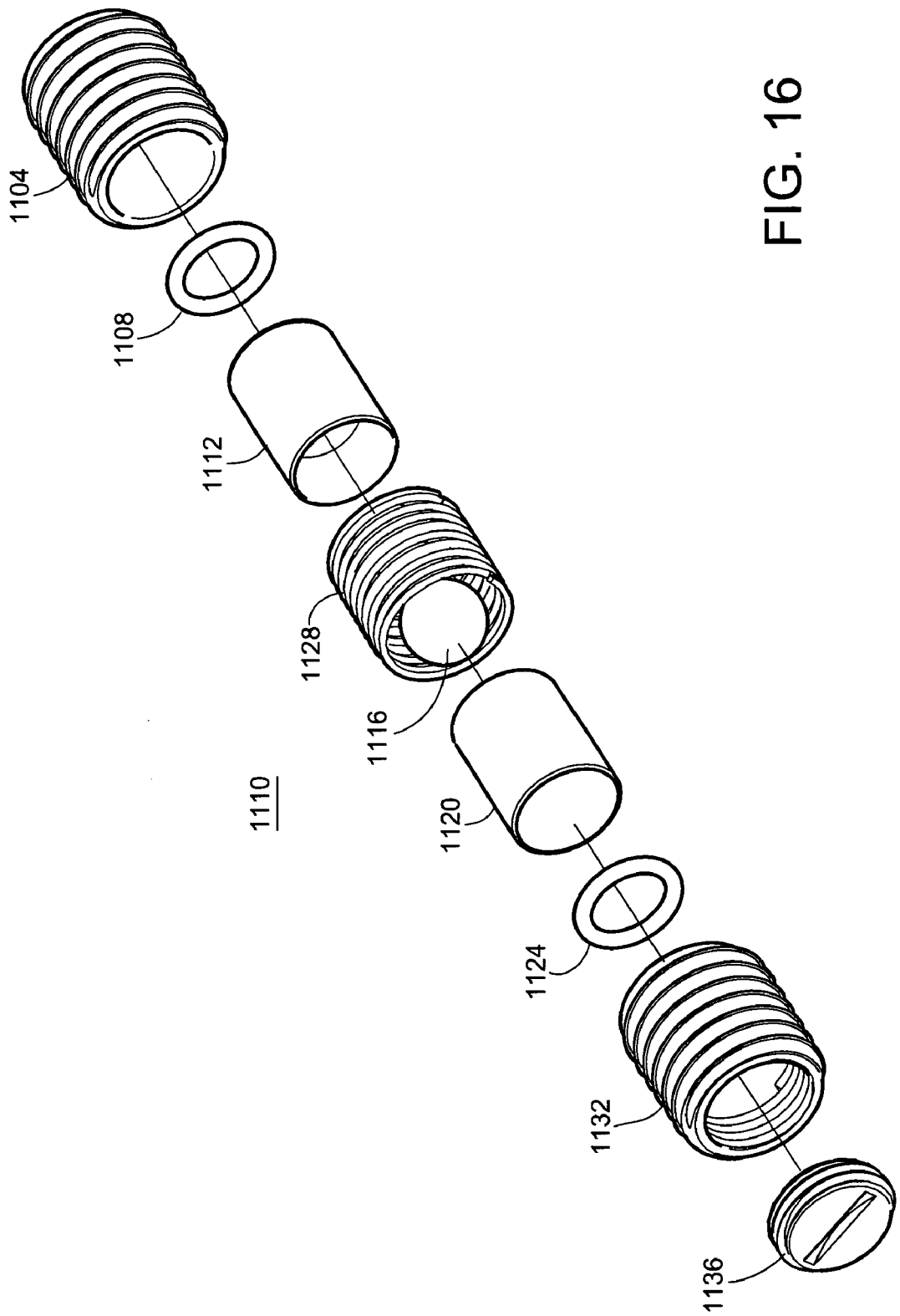
FIG. 16 shows the components of yet another motion preservation with a helical spring.

FIG. 16 shows the components of yet another motion preservation assembly 1100. This assembly has distal bone anchor 1104, distal O-ring 1108, distal pivot cup 1112, pivot 1116, proximal pivot cup 1120, proximal O-ring 1124, proximal bone anchor 1132, and end cup 1136. The interaction between these components is similar to the interaction between previously discussed components including the ability to impose a distraction based on the rotation of the end cup 1136 to axially advance within the proximal bone anchor 1132 through threaded engagement between the exterior of the end cup 1136 and the threaded interior of the proximal bone anchor 1132. An additional component in motion preservation assembly 1100 is a helical spring 1128 which in actual use would be connected between the distal end of the proximal bone anchor 1132 to the proximal end of the distal bone anchor 1104. The helical spring 1128 would be positioned in the intervertebral disc space of the motion segment receiving the motion preservation assembly 1100. This particular spring would not resist compressive loads as its low energy state is compressed. However, the helical spring 1128 would resist rotation of the motion preservation assembly 1100 in as the motion segment bends for flexure, extension, or lateral bending as any one of these movements while compressing one side of the helical spring would extend the opposite side of the spring.

FIG. 3 shows an implanted motion preservation assembly 300 which includes a prosthetic nucleus 348 which fills the intervertebral disc space 312 with an outer membrane 460 filled with prosthetic nucleus material 464. FIG. 3 should not be interpreted as a requirement that all motion preservation assemblies have a prosthetic nucleus or a particular type of prosthetic nucleus as motion preservation assemblies can be used with prosthetic nuclei created with barrier-sealant membranes as described below.

In prosthetic nucleus motion preservation assembly embodiments configured without expandable membranes, generally a two-step deployment process is used wherein a barrier-sealant membrane (BSM) is preferably first introduced through conformal contact with the interior surfaces of the intervertebral disc space to seal physiologic structures, e.g. fissures in the annulus, to preclude leakage of the subsequently introduced bulk prosthetic nucleus material. For prosthetic nucleus devices used as part of a motion preservation assembly, the viscoelastic properties, e.g., bulk and compressive moduli, are designed to substantially "match" those of the native disc nucleus, to functionally enable conformal contact of maximum device surface area within the intervertebral disc space; to "mimic" physiologic load distribution and dissipation; prevent bone erosion or implant subsidence; and exhibit sufficient resistance to fatigue and shear forces to preclude material fragmentation and migration out of the disc. In embodiments where the motion preservation assemblies are configured for use in conjunction with a barrier-sealant membrane, the barrier-sealant comprises aqueous solutions of synthetic or purified (non-antigenic) biopolymers or proteins, such as collagen or collagen-albumin mixtures or slurries; or fibrinogen, thrombin, and the like, or combinations thereof, of suitably highly fibrous; highly cross-linked; high density of solids (e.g., >65 mg/ml). In one embodiment, it is preferred that the biopolymer protein system be modified to be insoluble, and that proteins be of Type 1 when possible and appropriate. In another embodiment, the sealant additionally comprises a cross-linking agent, e.g., gluteraldehyde/aldehyde, or other suitable functional groups modified to minimize toxicity and/or necroses (e.g., citric-acid derivative).

In a preferred aspect of barrier-sealant membranes, the cross-linking agent(s) comprise(s) functionalities which reduce residuals or which are materials that are naturally metabolized. In one embodiment, the cross-linking agent comprises at least one citric acid derivative and synthetic or highly purified biopolymer or protein, such as systems as just described, (e.g., collagen; collagen-albumen; collagen; elastin, etc). In a preferred aspect, the cross-linker is a relatively low weight macromolecule comprising polar functional groups, such as carboxyl groups or hydroxyl groups, that are modified by means of electron attracting groups, e.g., succinimidyl groups.

In yet another embodiment, the barrier-sealant and/or barriers (e.g., thicker layers) comprise hydrocolloids. More specifically, the barrier-sealant membrane may be configured to comprise water soluble hydrophilic colloidal components, e.g., carboxymethylcellulose, in combination with elastomers or biopolymers as sealants or tissue repair matrices, respectively, and wherein the barrier membrane comprises non-degradable, semi-permeable film. In other embodiments, barriers may be pectin-based or foam.

The motion preservation assembly may be deployed without the concurrent creation of a prosthetic nucleus such as in situations where a prosthetic nucleus will not be deployed. The motion preservation assembly can be deployed in an assembly sequence that includes the insertion of an elastomeric ring or collar that abuts the annulus to prevent migration or leakage of prosthetic nucleus material or of the outer membrane through herniations and to dampen instantaneous load and to radially distribute loads to the annulus fibrosus.

To be more specific about the elastomeric ring or collar that abuts the annulus and serves to as a prosthetic annulus to dampen instantaneous load and to radially distribute loads to the annulus fibrosis, a non-inflatable elastomeric (e.g., silicone or polyurethane) collar, can be used in conjunction with the expanding membrane. This collar is described in U.S. Provisional Application 60/558,069 for Axially-Deployed Spinal Mobility Devices and has is incorporated by reference herein. This collar is first deployed by folding until delivered to the intervertebral disc space. The collar is configured to conform with, i.e., buttress the annulus to prevent migration or leakage of the membrane through herniations. The cross sectional area of the collar is stiffer, relative to the expandable membrane. In a preferred embodiment the collar is from between about 8 mm-12 mm high and about 0.5 to 1.0 mm thick.

An alternative way to reinforce the annulus is to use an expandable outer membrane between the distal anchor section and the proximal anchor section (in lieu of outer membrane 460 discussed above) where the outer membrane when expanded places membrane material against the annulus fibrosus that is stiffer than the membrane material placed near the endplates of the proximal and distal vertebral bodies.

This annulus reinforcing outer membrane may be deployed alone or in combination with an elastomeric ring or collar that abuts the annulus, wherein the motion preservation assembly device effectively functions as a prosthetic disc (PD) and provides the same load-bearing characteristics as the natural disc, without undergoing the invasiveness of current total disc replacement (TDR) procedures. The balance of compliancy and stiffness, i.e., the addition of the semi-compliant, elastomeric component, whether provided as a collar and/or an outer membrane for a prosthetic nucleus with an integral stiffer component as previously described, enables the motion preservation assemblies to cushion a motion segment, without collapsing under compressive load. That is, the semi-compliant component provides dampening of instantaneous load, and also maintains effective surface area of conformal contact (congruent interface) between the motion preservation assembly and the physiological structures, i.e., the annulus and the end plates for the proximal and distal vertebral bodies. In turn, this yields a more uniform, radial distribution of loads to more closely approximate physiological load sharing. In accordance with this aspect of the present invention, the mobility devices disclosed herein are less likely to cause the phenomena of subsidence and/or transition syndrome.

Preferred Materials

In a preferred aspect of the present invention, the non-elastomeric components motion preservation assembly of the present invention are configured to preferably comprise biocompatible, high-strength materials, e.g., MP35N; Co—Cr alloy such as Stellite™. In the context herein, "biocompatible" refers to an absence of chronic inflammatory response when or if physiological tissues are in contact with, or exposed to (e.g., wear debris) the materials and devices of the present invention. In addition to biocompatibility, in another aspect of the present invention it is preferred that the materials comprising the motion preservation assembly, are sterilizable; visible and/or imageable, e.g., fluoroscopically; or via CT (computed tomography), or MRI (magnetic resonance imaging), with this last-named imaging technique mandating that materials be substantially free of Fe (iron). Moreover, in consideration of contrast, detail, and spatial sensitivity, it is contemplated that contrast media or other materials (e.g., barium sulfate) may be employed in configuring devices when and where needed and appropriate, to supplement or modify radiolucency or radio-opaqueness. Also, as used herein, high-strength means that it is preferred that exemplary embodiments' materials generally meet ISO 10993 standards for long-term implants, and/or are able to withstand, without wear, long term normal ranges of physiological loading (i.e., over the lifetime of the implant, or up to about $40 \times 10^6$ cycles) of between about 1250 Newtons (N) (280 lbf) and 2250N (500 lbf) axial compression; 100 N (25 lbf) and 450N (100 lbf) of both lateral and sagittal shear, respectively, through full ROM. Additionally, the motion preservation assemblies of the present invention are preferably able to tolerate short term (e.g., over about 20 continuous cycles) maximum physiological loads through full ROM of about 8000 Newtons (N) (1800 lbf) axial compression; about 2000 N (450 lbf) lateral shear; and about 3000 N (675 lbf) sagittal shear, without failing.

In a preferred embodiment, the pivot and the bearing surfaces are Co—Cr alloy such as Stellite™. Moreover, the ends of the pivot can be treated (e.g., surface or heat treatments as appropriate) to enhance wear resistance. Thus while the chemical composition may be the same the ends are now a different material from the middle as in this context "material" is a combination of the composition and treatments to produce properties. In yet another embodiment, the pivot body may be made of another compatible material (e.g., one that will not react so as to cause electrochemical corrosion) so that while the pivot ends are made more wear resistant, the material used for the pivot body and or the pivot body may be treated to enhance fatigue resistance relative to the material used for the pivot ends. Having the pivot made from two pivot ends and a pivot body rather than machined from a single piece of metal is not an unreasonable manufacturing strategy even if the ends and body are made from the same material, e.g., highly polished, highly round, spheres that are available commercially. A preferred material for the retainer ring 484 is titanium.

Details on Process to Install a Motion Preservation Assembly.

A co-pending and commonly assigned U.S. Provisional Application No. 60/621,730 filed Oct. 25, 2004 for Multi-Part Assembly for Introducing Axial Implants into the Spine has been claimed as a priority document and incorporated by reference into this application. Details about tooling and methods for installing motion preservation assemblies are found in that application.

As it may be useful to see the interaction of the motion preservation assembly with various drivers, a sequence of steps are set forth below with emphasis on how the driver interacts with the motion preservation assembly rather than on details of the construction of the driver devices.

Figure 17:
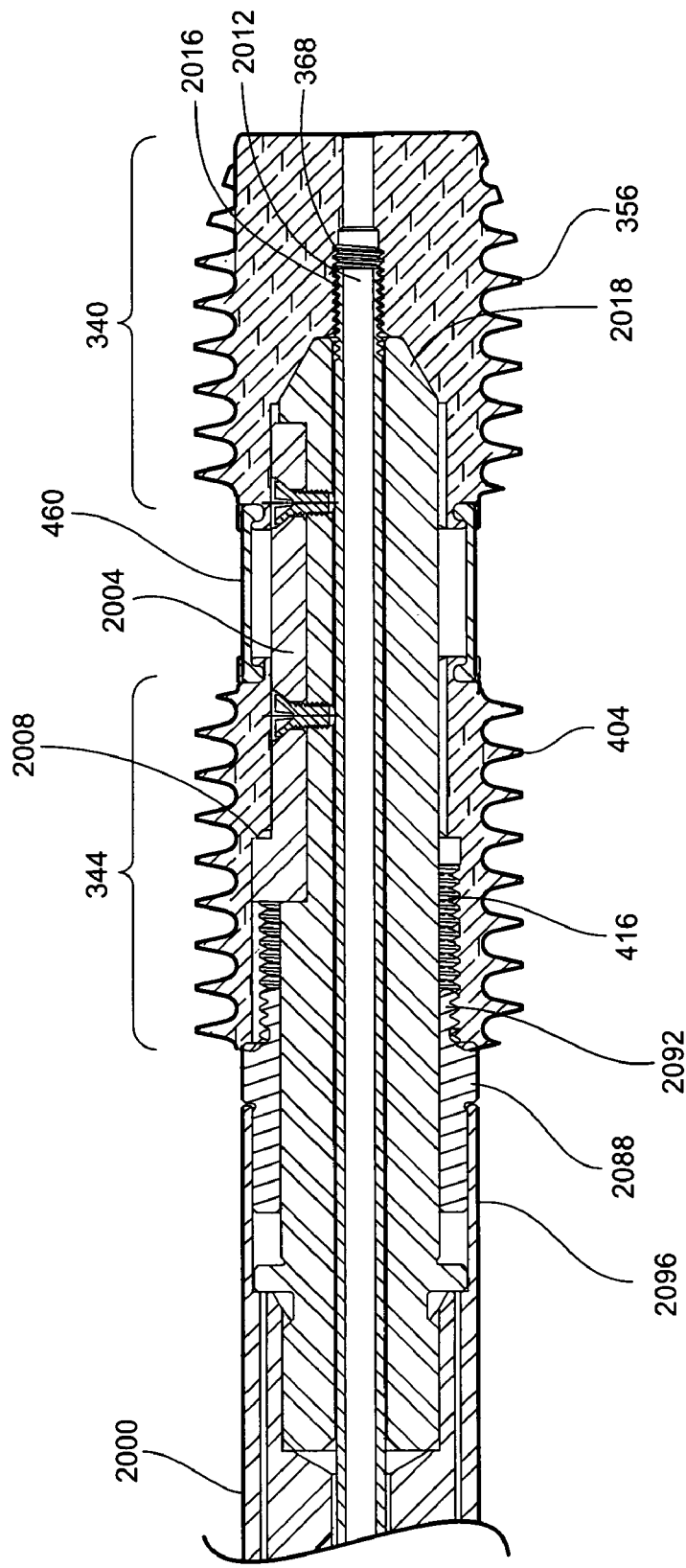
FIG. 17 shows the cross section of a keyed driver assembly for delivery of two implanted components.

FIG. 17 shows a distal bone anchor 340 and a proximal bone anchor 344 with a membrane 460 connected to the distal bone anchor 340 and the proximal bone anchor 344. In this example, the thread pitch of the external threads 356 on the distal bone anchor are the same as the thread pitch on the set of external threads 404 on the proximal bone anchor. The keyed driver assembly 2000 has a key 2004 with a shoulder 2008. The key 2004 slides in the slots in the proximal bone anchor and the distal bone anchor (previously discussed). The keyed driver assembly 2000 thus prevents the proximal bone anchor 344 from rotating relative to the distal bone anchor 340. Keying along with precise control of the distance between the bone anchors allows the leading edge of the external thread on the proximal bone anchor to enter into the proximal vertebral body into the beginning of the thread path left by the distal bone anchor as it was screwed up through the proximal vertebral body while moving towards the distal vertebral body.

A retention rod 2012 with external thread 2016 engages with the internal threaded section 368 of the distal bone anchor 340. The retention rod 2012 can be rotated relative to the driver tip 2018 so that the distal bone anchor 340 is pulled to contact the driver tip 2018.

Likewise a proximal anchor retention coupler 2088 with external threads 2092 can rotate relative to the driver tip 2018 as the proximal anchor retention coupler 2088 is attached to an external sheath 2096. Rotation of the proximal anchor retention coupler 2088 causes engagement between the external threads 2092 and the internal threads 416 of the proximal anchor 344 to draw the proximal anchor 344 down onto the shoulder 2008. With both anchors retained in contact with components of the keyed driver assembly 2000 the position of the distal bone anchor 340 relative to the proximal bone anchor 344 can be set based on the distances between the shoulder 2008 and the driver tip 2018. Control over the distances between the two separate bone anchors allows the two bone anchors with the same major diameter to be inserted without cross threading of the proximal vertebral body.

Figure 18:
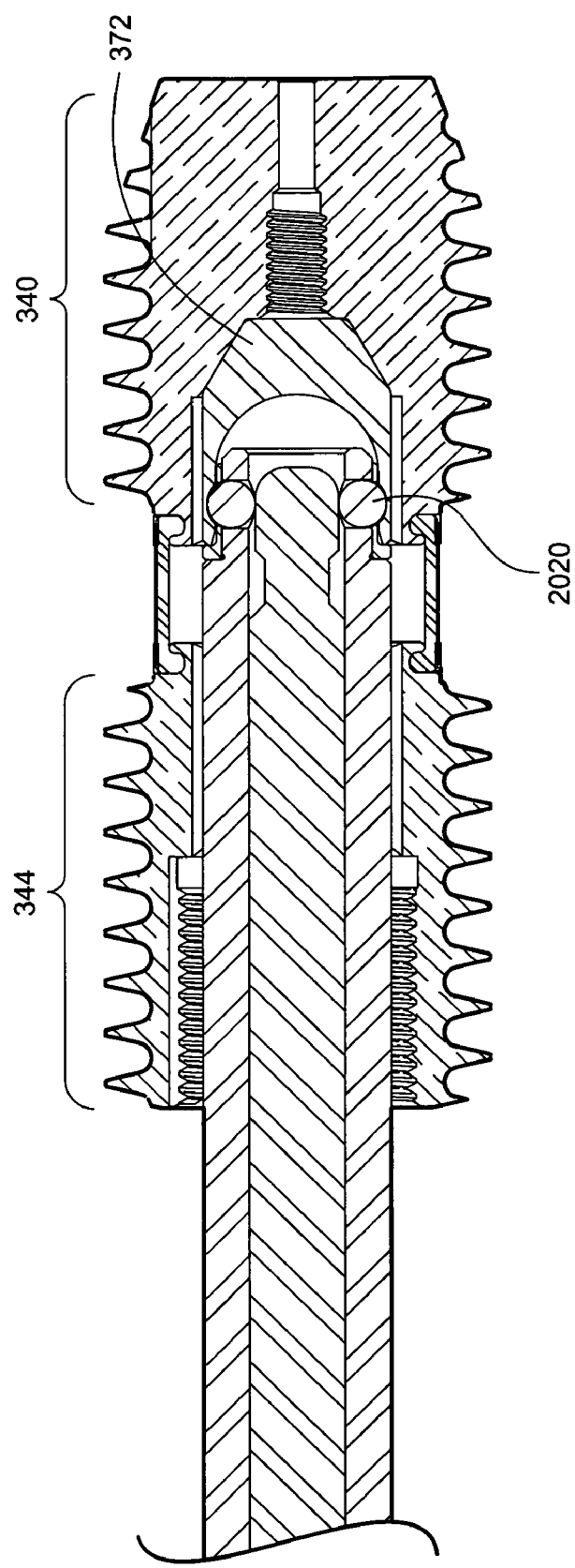
FIGS. 18 and 19 show the cross section of a delivery tool during the delivery of the distal pivot cup.
Figure 19:
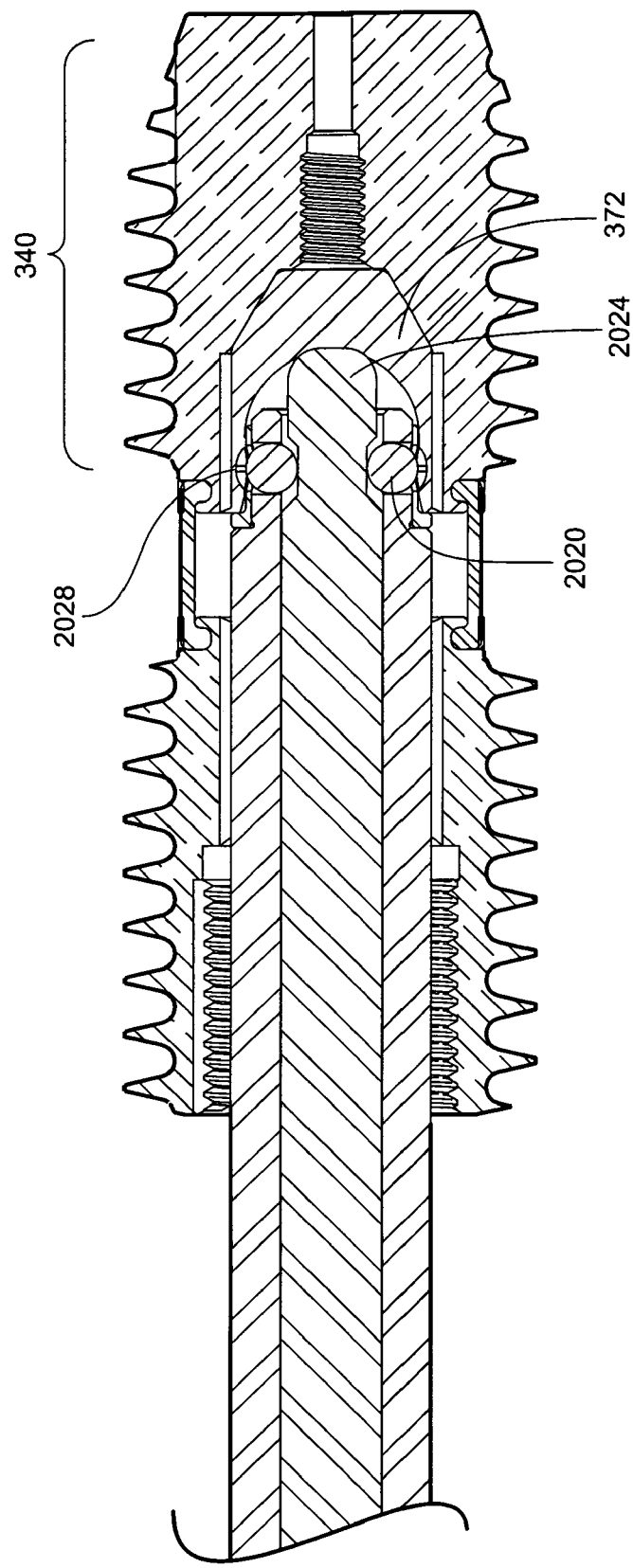

FIG. 18 shows the delivery of the distal pivot cup 372 within distal bone anchor 340 by a distal cap driver 2022 using a set of detent protrusions 2020 to engage detent concavities (See element 2028 in FIG. 19). FIG. 19 shows the disengagement of the driver by the extension of an atraumatic tip 2024 to cause the axial motion of the driver away from the distal end of the distal end cup 372 so that the detent protrusions 2020 disengage from the detent concavities 2028. In one embodiment, the atraumatic tip 2024 is selected to be softer than the bearing surface in the distal end cup 372 so that that bearing surface is not scratched or marred.

Figure 20:
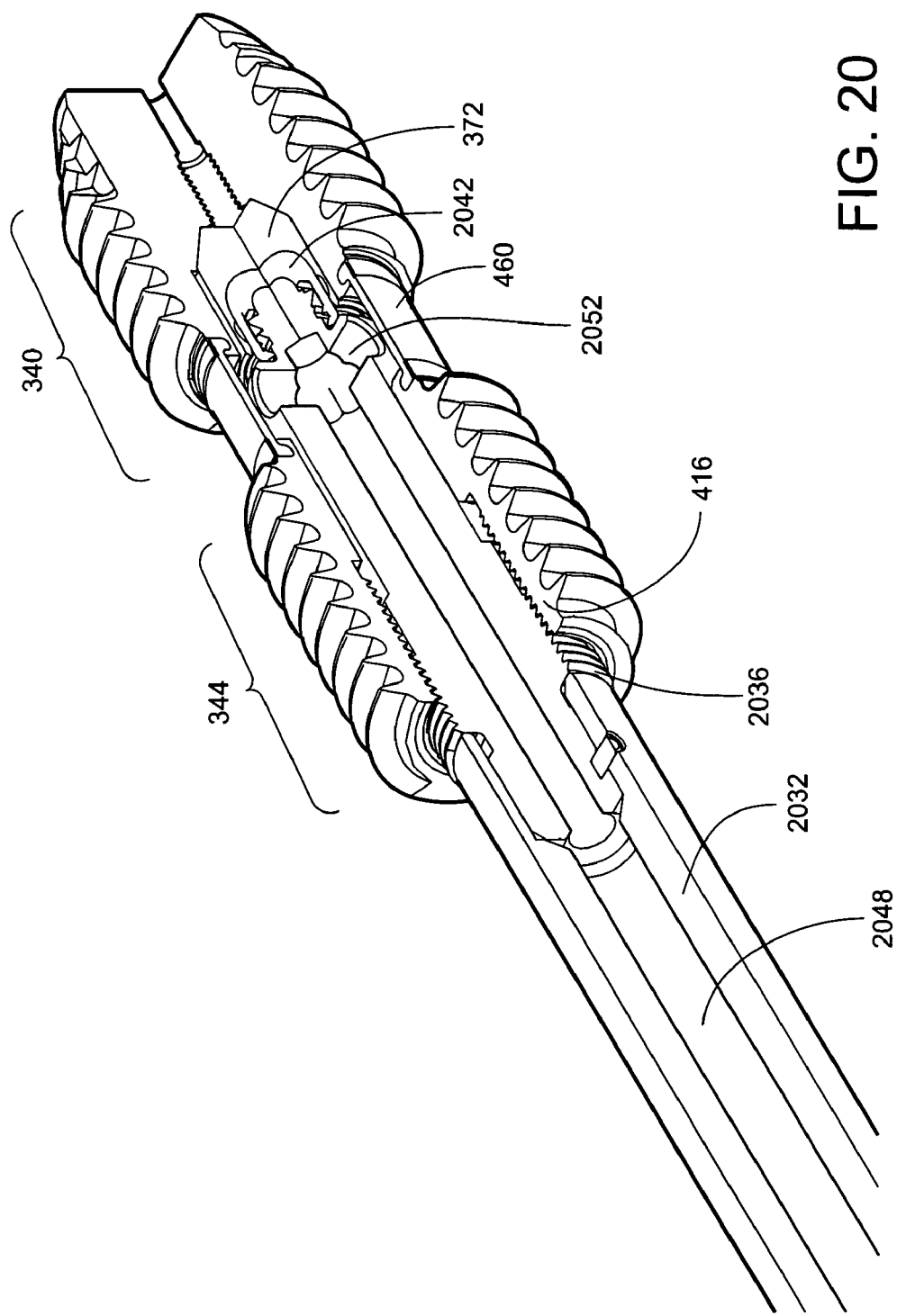
FIG. 20 shows a perspective view with a quarter round removed from a distractor/injector tool.

FIG. 20 shows a distraction and insertion tool 2032 used to distract the motion segment then deploy prosthetic nucleus material in to the membrane 460 to distend the membrane 460 to a conforming fit within the space of the intervertebral disc space. The insertion tool 2032 has a set of external threads 2036 which engage with a set of internal threads 416 in the proximal bone anchor 344. The distal end of the insertion tool 2032 is an atraumatic tip 2042 designed to contact without damaging the bearing surface in the distal pivot cup 372. Axially advancing the distraction and insertion tool 2032 pushes the atraumatic tip 2042 on the distal pivot cup 372 to move the vertebral body engaged with the distal bone anchor 340 relative to the vertebral body engaged with the proximal bone anchor 344. After achieving the desired amount of distraction an internal channel 2048 is used to provide prosthetic nucleus material to be delivered through a set of fenestrations 2052 to fill and expand the membrane 460. The prosthetic nucleus material is inserted until there is a conforming fit between the membrane 460 and the endplates of the two vertebral bodies and the wall of the annulus fibrosus.

After the prosthetic nucleus material is allowed to cure, the insertion tool 2032 can be removed leaving behind a void in the prosthetic nucleus material where the insertion tool was during the formation of the prosthetic nucleus. (see element 348 on FIG. 3). As the sequence of drawings show a device that is not implanted in a motion segment, the non-implanted device shown in FIG. 20 did not actually received prosthetic nucleus material. An astute observer will note that subsequent Figures in this sequence do not show an expanded membrane.

Figure 21:
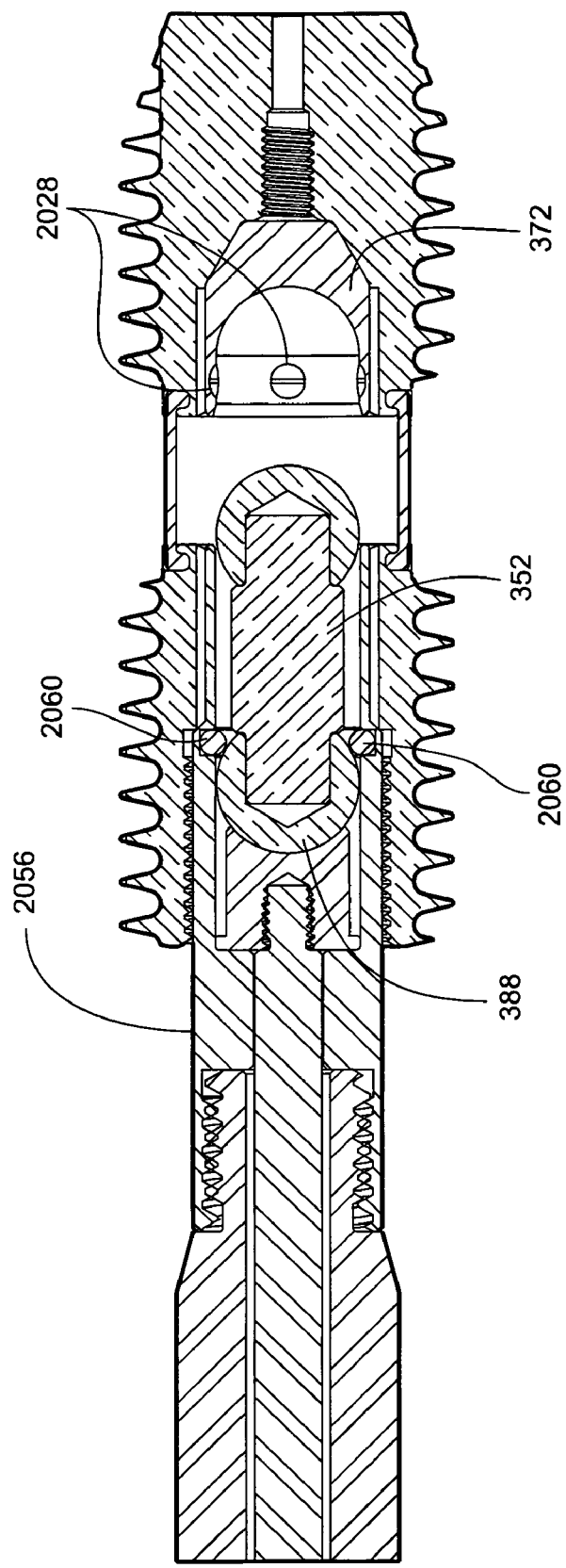
FIGS. 21 and 22 show the cross section of a delivery tool during the delivery of a dual pivot to the distal pivot cup.
Figure 22:
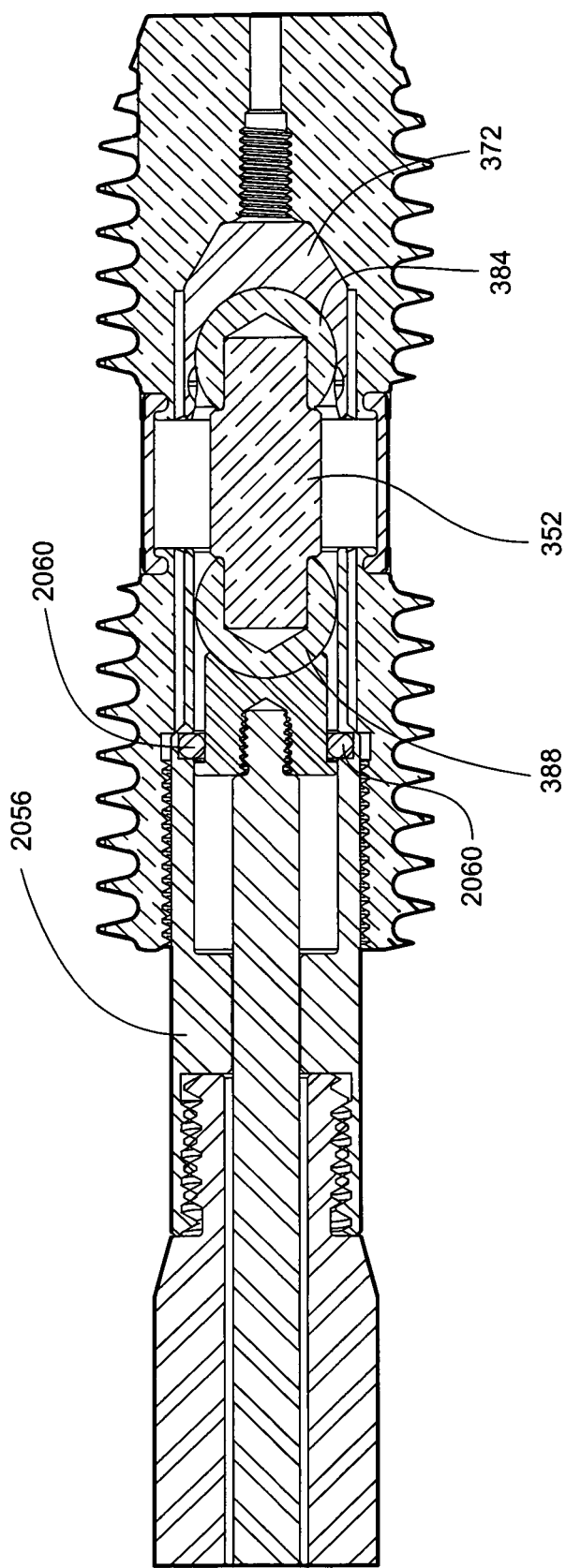

FIG. 21 show the delivery of a pivot 352 by delivery tool 2056 which engages the pivot's proximal end 388 by an O-ring 2060. FIG. 22 shows the pivot 352 after delivery with pivot's distal end 384 in contact with the bearing surface in the distal pivot cup 372 and the pivot's proximal end 388 pushed beyond the O-ring 2060. The delivery of the pivot 352 would not be impeded by the cured prosthetic nucleus material as this material would not have cured along the central axis of the motion preservation device as the insertion tool 2032 occupied that volume during the filling and curing. To the extent that compressive forces on the prosthetic nucleus have resulted in some movement of prosthetic nucleus material towards the longitudinal centerline of the motion preservation assembly, the pivot 352 can be pushed through the reduced opening by displacing the flexible prosthetic nucleus material.

Figure 23:
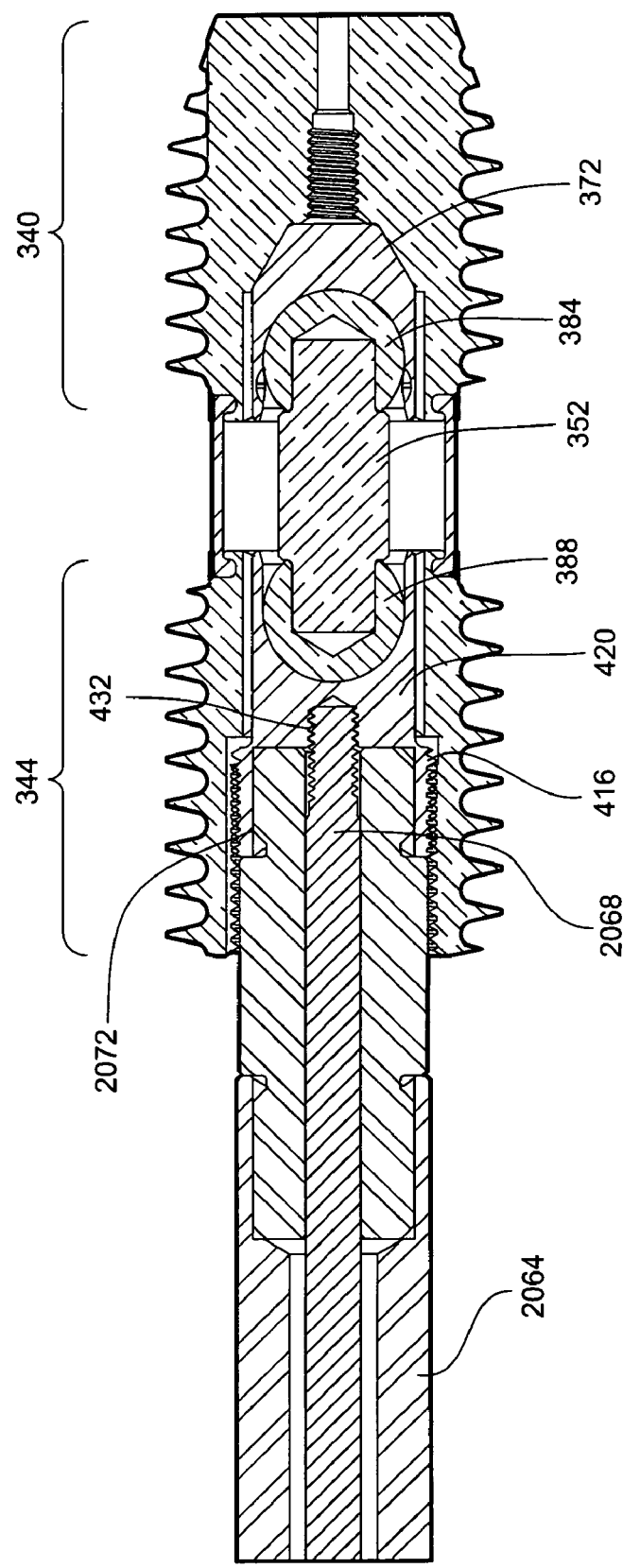
FIG. 23 shows the cross section of a delivery tool during the delivery of a proximal end cup.

FIG. 23 shows the use of a driver 2064 that is engaged with proximal pivot cup 420 by retaining rod 2068 which is threadedly engaged with the threaded cavity 432 in the proximal pivot cup. A driver head 2072 engages the corresponding driver engagement section 428 (best seen in FIG. 3) in the proximal pivot cup 420 to apply torque to axially advance the proximal pivot cup 420 within the proximal bone anchor 344 and thus to push via the pivot 352 on the distal pivot cup 372 and thus on the distal bone anchor 340 to move the distal bone anchor 340 relative to the proximal bone anchor 344. When implanted in vertebral bodies, this would move the vertebral bodies apart to impose an axial distraction.

Figure 24:
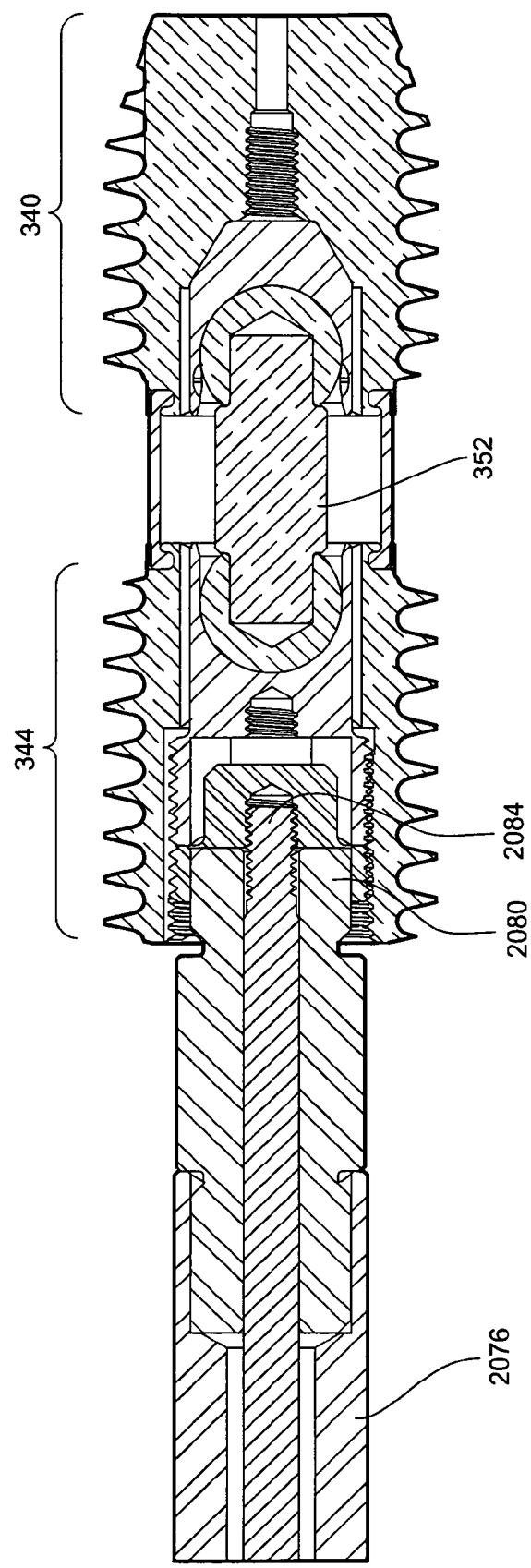
FIG. 24 shows the cross section of a delivery tool during deliver of a jam nut.

A comparison of FIG. 23 and FIG. 24 illustrates the concept of the movement of the components such that the pivot 352 is more closely centered between the distal bone anchor 340 and the proximal bone anchor 344. As previously mentioned, the pivot 352 can be provided in a variety of lengths so that a pivot 352 is properly oriented with respect to the intervertebral space after an imposed distraction.

FIG. 24 shows a jam nut driver 2076 with a driver head 2080 and a retention rod 2084 to engage the jam nut through threaded cavity 352 (best seen in FIG. 3) and driver engagement section 448 (best seen in FIG. 3).

Figure 25:
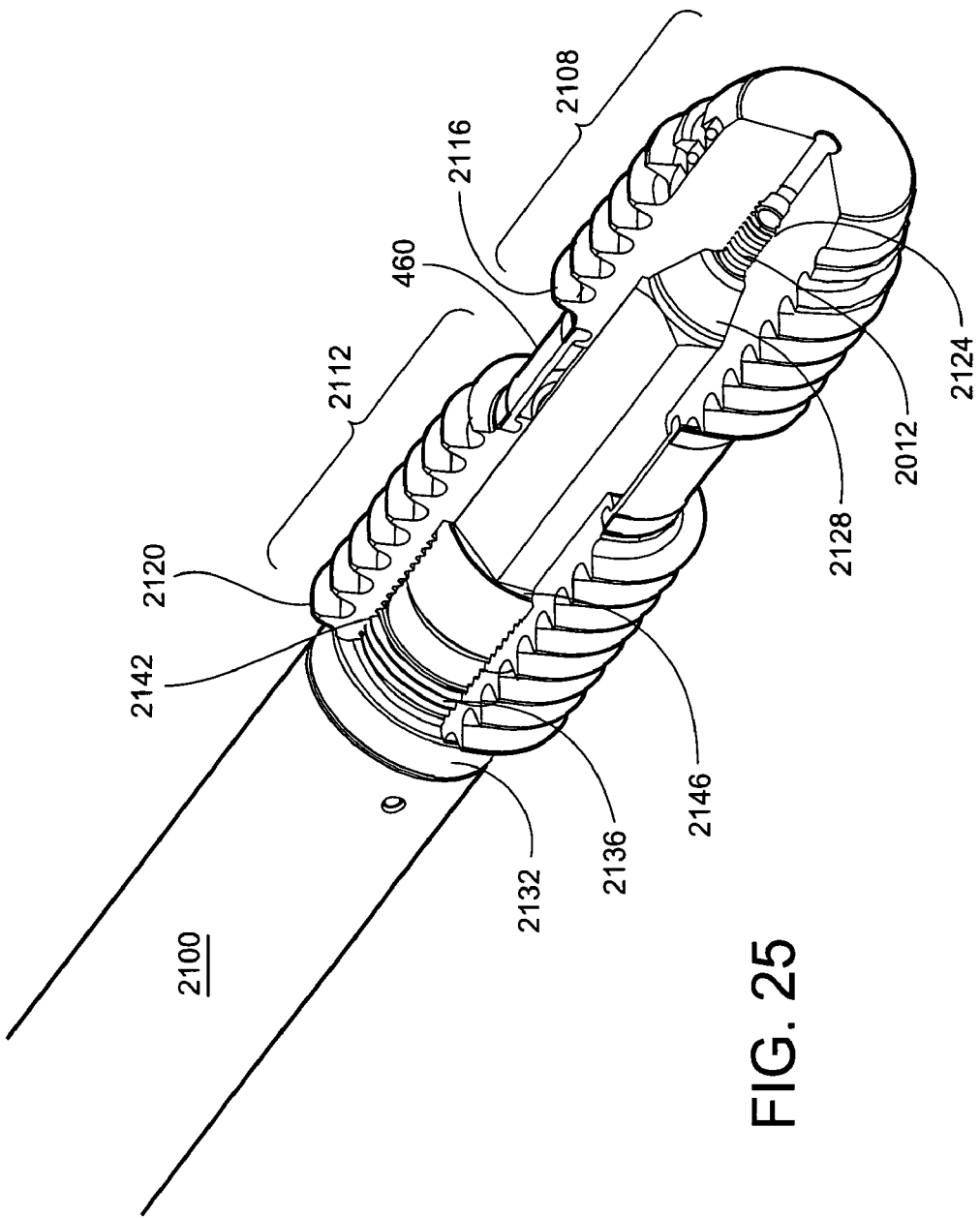
FIG. 25 shows the perspective view of the distal portion of a driver assembly for delivery of two implanted components using an elongated hexagonal driver.
Figure 26B:
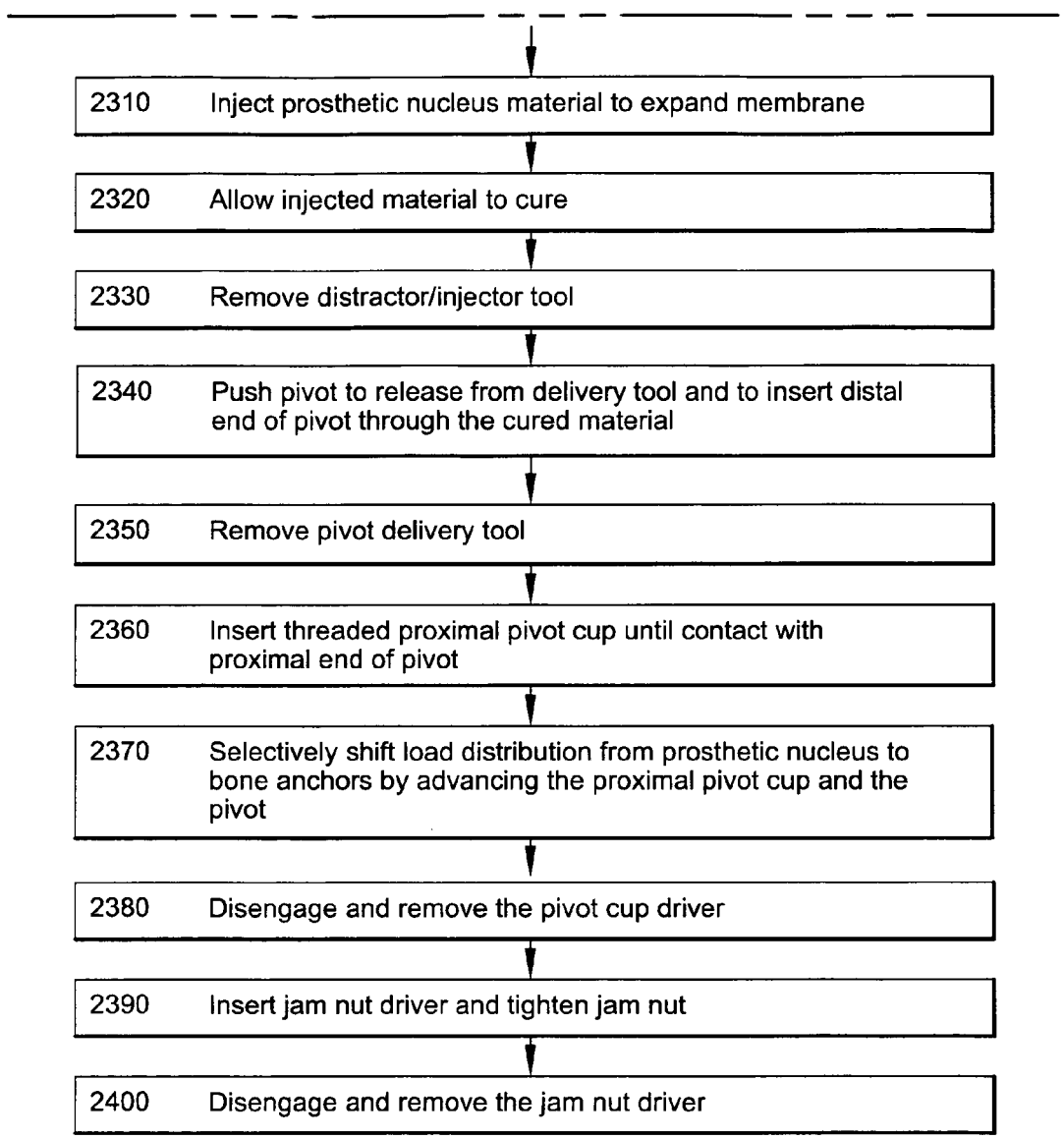
FIG. 26 is a flow chart describing a particular method for deployment of a motion preservation assembly.

FIG. 25 provides an alternative to the keyed driver assembly 2000 shown in FIG. 17. The dual anchor driver 2100 uses a polygonal torque driver 2104 to simultaneously engage a distal bone anchor 2108 and a proximal bone anchor 2112. These bone anchors have external threaded sections (2116 and 2120) that have the same minor diameter, the same major diameter, the same pitch, and the same handedness. In order to avoid cross threading the helical thread cut left by distal anchor external threads 2116 in the proximal vertebral body as the proximal anchor external threads 2120 are rotated into the proximal vertebral body, the delivery of the two bone anchors must be timed. Having control over the relative position of the bone anchors during the rotation and axial advancement of the bone anchors makes this possible. Here the control is provided by A) the action of retention rod 2012 engaging with internal threads 2124 of distal anchor 2108 to pull the distal anchor 2108 to seat it on the distal tip 2128 of the polygonal torque driver 2104 and B) the action of proximal anchor retention coupler 2132 engaging a set of external threads 2136 with internal threads 2142 of proximal anchor 2112 to seat the proximal anchor 2112 on a shoulder 2146 polygonal torque driver 2104. Both retention rod 2012 and proximal anchor retention coupler 2132 are connected to dual anchor driver 2100 such that each can rotate relative to the polygonal torque driver 2104.

Although not readily visible in FIG. 25, a dual anchor driver 2100 using a polygonal torque driver 2104 does not need to interact with slots in the bone anchors as is necessary when using the keyed driver of FIG. 17. One of skill in the at will recognize that while a hexagonal polygon is commonly used as a torque driver, other polygons could be used such as triangular, square, pentagonal, octagonal and so on. More complex shapes such as stars or non symmetric shapes could be used but a simple polygon is adequate.

Those of skill in the art will appreciate that other relationships between the driver and the two bone anchors can result in timed delivery of the proximal bone anchor to the thread path cut in the proximal vertebral body by the distal bone anchor. One such solution is to use a double-hex head driver such as a double-hex head hex driver with a hex head that engages a corresponding driver engagement section in the cavity of the distal bone anchor, a spacer shaft connected to the top hex head and extending from a larger lower hex head that engages with the interior walls of the proximal bone anchor. As the distal bone anchor and the proximal bone anchor would be preloaded onto the double hex driver and retained there (such as with a retainer rod and threaded retention coupler) until implanted in the vertebral bodies, the orientation of the two bone anchors could be controlled as the rotation orientation and relative axial position will not change while the bone anchors are in contact with the double-hex head.

A double-hex driver with a smaller distal head is appropriate when the distal bone anchor is narrower than the proximal bone anchor such as when dissimilar thread pitch is being used for distraction. However, dissimilar thread pitch is not the preferred means for distraction.

Preferred Method of Deployment and Use

While the present invention can be implemented with a number of variations as described above and these variations impact the steps for implantation, it is instructive to summarize the deployment steps 2200 for a preferred motion preservation assembly (MPA) and prosthetic disc replacement, that is one with vertebral implant distal component and a proximal component having the same rod diameter and external threads of the same major diameter, minor diameter, thread pitch, and handedness such that it is necessary to have a timed delivery of the proximal component to enter the helical thread path cut into the proximal vertebral body by the passage of the distal component, said threaded components serve to anchor the implants in adjacent vertebral bodies. This embodiment uses a flexible membrane that is configured to be intermediate to and integral with the distal component to the proximal component and is later expanded with insertion of prosthetic nucleus material to form a prosthetic nucleus component within the intervertebral disc space between the adjacent distal and proximal vertebral bodies.

The preferred driver for two threaded components of the same diameter (such as just described above) is an elongated hex driver analogous to that shown in FIG. 25. As many details about the bone anchors and the drivers have previously been introduced, this flow chart serves as a summary rather than a detailed introduction.

Step 2210 Load the device driver assembly with both the distal and proximal components. These two anchors, connected by a flexible membrane, are placed on the anchor driver assembly. The driver assembly is analogous to the anchor driver assembly in FIG. 25 in that it uses an elongated torque driver, in this case a hexagonal shaped-toque driver with an elongated section with a constant cross sectional (taken perpendicular to the longitudinal axis).

The step of loading the driver assembly includes seating the distal component onto the distal end of the driver wherein it is retained on the tip during insertion and axial, distal advancement by means of a threaded retention rod, and seating the proximal bone anchor on a shoulder within the dual anchor driver assembly through use of a proximal anchor retention coupler. Seating the two bone anchors on the driver assembly maintains a predetermined spatial separation between the distal component and proximal component and stretches the flexible membrane located therebetween so that the membrane slightly "necks in" and is less likely to be damaged while passing through the proximal vertebral body.

Step 2220 Insert the anchor driver assembly over a guide wire and advance the anchor driver assembly through the previously prepared axial channel that includes a bore through the proximal vertebral body and a bore in the distal vertebral body. The bore hole in the proximal vertebral body is about the size of the minor diameter of the external threads on both bone anchors.

Step 2230 Torque is applied using the anchor driver assembly to rotate and axially advance the distal bone anchor through the proximal vertebral body thereby creating a helical thread path through the first vertebral body.

Step 2240 Continued application of torque axially advances the bone anchors, which are held on the anchor driver assembly at a spatially maintained distance, to anchor the distal component into the distal vertebral body and anchor the proximal component into the proximal vertebral body without cross threading or rethreading in the proximal vertebral body.

Step 2250 Once the bone anchors are positioned into the respective vertebral bodies, release the distal bone anchor from the threaded engagement with the retention rod and release the proximal bone anchor from the proximal anchor retention coupler as the retention rod and the proximal anchor retention coupler can be rotated relative to the elongated hexagonal hex driver.

Step 2260 Remove the anchor driver assembly.

Step 2270 Insert the distal pivot cup by engaging the distal pivot cup with driver such as show in FIGS. 18 and 19 that employs a detent mechanism to engage the distal pivot cup.

Step 2280 Disengage the distal pivot cup driver from the distal pivot cup and remove the distal pivot cup driver.

Step 2290 Insert distractor/injector tool into the implanted bone anchors so that atraumatic tip of the distractor/injector tool contacts the distal pivot cup bearing surface.

Step 2300 Move the distal vertebral body relative to the proximal vertebral body by axially advancing the distractor/injector tool relative to the proximal bone anchor through threaded engagement within the proximal bone anchor to push via an atraumatic tip on the distal pivot cup.

Step 2310 Inject prosthetic nucleus material through the interior of the distractor/injector and out apertures in fluid communication between the interior of the distractor/injector and the flexible membrane to expand and fill the flexible membrane sufficiently to form the prosthetic nucleus component of this prosthetic disc device, the prosthetic nucleus component being in conformal contact with the surfaces of the intervertebral disc space.

Step 2320 Allow the injected material to cure.

Step 2330 Remove the distractor/injector tool.

Step 2340 Engage the proximal end of the pivot with delivery tool. Insert delivery tool and push the distal end of the pivot through the cured material and into the distal pivot cup while releasing the proximal end of the pivot from the engagement with the delivery tool. A preferred delivery tool is shown in FIGS. 21 and 22.

Step 2350 Remove the pivot delivery tool from the axial channel.

Step 2360 Insert the threaded proximal pivot cup into the proximal bone anchor. Engage the threads in the proximal bone anchor and advance the proximal pivot cup to contact the proximal end of the pivot.

Step 2370 Further rotation and axial advancement of the proximal pivot cup pushes the pivot against the distal pivot cup and thus causes additional incremental distraction of the distal vertebral body relative to the proximal vertebral body. The ability to additionally adjust distraction of the vertebral bodies in this manner enables selective distribution of axial load bearing between the prosthetic nucleus component of the prosthetic disc device, and the mechanical "in-line" sub-assembly comprising the pivot, bearing surface, elastomeric component, and the distal and proximal threaded components anchored in the vertebral bodies. This distraction imposes a compressive force on the one or more components that can undergo an elastic deformation in compression.

Step 2380 Disengage driver from pivot cup

Step 2390 Engage jam nut with driver. Insert driver and jam nut into the axial channel. Engage the threads on the jam nut with threads on the proximal bone anchor and tighten. The preferred process uses the same driver for the pivot cup and the jam nut.

Step 2400 Disengage the driver from the jam nut and remove the driver from the axial channel.

While this ends the process of deploying a motion preservation device in an axial channel in the spine, the surgical site would be closed by a surgeon.

One of skill in the art will recognize that the alternative embodiments set forth above are not universally mutually exclusive and that in some cases alternative embodiments can be created that employ two or more of the variations described above. Likewise, the present invention is not limited to the specific examples or particular embodiments provided to promote understanding of the present invention. Moreover, the scope of the present invention covers the range of variations, modifications, and substitutes for the components described herein as would be known to those of skill in the art.

The legal limitations of the scope of the claimed invention ares set forth in the claims that follow and extend to cover their legal equivalents. Those unfamiliar with the legal tests for equivalency should consult a person registered to practice before the United States Patent and Trademark Office.

The invention claimed is:

1. A spinal motion preservation assembly adapted for assembly in a spinal motion segment the spinal motion preservation assembly comprising:
   a distal bone anchor comprising:
      a distal end;
      a proximal end;
      a cavity in an interior of the distal bone anchor accessible from the proximal end, the cavity adapted for receipt of a distal pivot cup inserted into the proximal end of the distal bone anchor; and
      a set of threads on an exterior of the distal bone anchor, the set of threads adapted to engage a distal vertebral body in the spinal motion segment;

a pivot comprising:
- a distal end;
- a proximal end; and
- a middle between the distal end and the proximal end;

the distal pivot cup comprising:
- an exterior corresponding to a portion of the cavity in the interior of the distal bone anchor; and
- a cavity at the proximal end of the distal pivot cup for receiving the distal end of the pivot;

a proximal bone anchor comprising:
- a distal end;
- a proximal end;
- a cavity that runs through an interior of the proximal bone anchor from the distal end to the proximal end, the cavity adapted for receipt of a proximal pivot cup inserted into the proximal end of the proximal bone anchor; and
- a set of threads on the exterior of the proximal bone anchor adapted to engage a proximal vertebral body in the spinal motion segment;

a proximal pivot cup comprising:
- a distal end;
- a proximal end; and
- a cavity at the distal end of the proximal pivot cup for receiving the proximal end of the pivot;

at least one component located between the distal end of the distal bone anchor and the proximal end of the proximal bone anchor that is elastically deformable; and the distal bone anchor, distal pivot cup, pivot, proximal pivot cup, and proximal bone anchor all adapted for insertion from a bore in the proximal vertebral body in the motion segment such that the spinal motion preservation assembly may be inserted and assembled in the spinal motion segment through use of just the bore in the proximal vertebral body.

2. The spinal motion preservation assembly of claim 1 wherein the cavity in the distal bone anchor extends from the proximal end to the distal end along the longitudinal axis such that the distal bone anchor can be deployed over a guide wire.

3. The spinal motion preservation assembly of claim 1 wherein the spinal motion preservation assembly is adapted such that the spinal motion preservation assembly could, if implanted in a spinal motion segment, move in flexion, extension, lateral bending to the right, lateral bending to the left, clockwise axial rotation, and counterclockwise axial rotation.

4. The spinal motion preservation assembly of claim 3 wherein the spinal motion preservation assembly is adapted such that the spinal motion preservation assembly could, if implanted in a spinal motion segment move in about 12 degrees of flexion, about 8 degrees of extension, about 9 degrees of lateral bending to the right, about 9 degrees of lateral bending to the left, about 2 degrees of clockwise axial rotation, and about 2 degrees of counterclockwise axial rotation.

5. The spinal motion preservation assembly of claim 4 wherein the spinal motion preservation assembly is adapted such that the spinal motion preservation assembly could, if implanted in a spinal motion segment allow the distal vertebral body to translate relative to the proximal vertebral body in the anterior/posterior direction and in the lateral right/lateral left direction as well as translation arising from the elastic deformation and recovery of at least one component of the spinal preservation assembly.

6. The spinal motion preservation assembly of claim 1 wherein at least one component that can undergo elastic deformation is made from a material selected from the group consisting of fluoropolymer elastomer, polyurethane elastomer, and silicone rubber.

7. The spinal motion preservation assembly of claim 1 wherein at least one component that can undergo elastic deformation is a spring adapted to recoverably deform in compression.

8. The spinal motion preservation assembly of claim 1 wherein at least one component that can undergo elastic deformation is located between the distal pivot cup and the distal bone anchor.

9. The spinal motion preservation assembly of claim 1 wherein at least one component that can undergo elastic deformation is located between the proximal pivot cup and the proximal bone anchor.

10. The spinal motion preservation assembly of claim 1 wherein at least a portion of the pivot can undergo elastic deformation.

11. The spinal motion preservation assembly of claim 10 wherein the pivot is at least partially comprised of a fabricated spring.

12. The spinal motion preservation assembly of claim 1 wherein at least a portion of the distal pivot cup can undergo elastic deformation.

13. The spinal motion preservation assembly of claim 12 wherein the distal pivot cup is at least partially comprised of a fabricated spring.

14. The spinal motion preservation assembly of claim 1 wherein at least a portion of the proximal pivot cup can undergo elastic deformation.

15. The spinal motion preservation assembly of claim 14 wherein the proximal pivot cup is at least partially comprised of a fabricated spring.

16. The spinal motion preservation assembly of claim 1 wherein the pivot is comprised of:
- a material having a first set of biomechanical properties optimized for wear and that is used in configuring the distal end and the proximal end, and
- a material having a second set of biomechanical properties optimized for fatigue resistance and that is used in configuring the pivot body between the distal end and the proximal end.

17. The spinal motion preservation assembly of claim 1 further comprising a flexible intermediate section connected to the proximal end of the distal bone anchor and the distal end of the proximal bone anchor so that a range of movement of the distal vertebral body relative to the proximal vertebral body along the longitudinal axis of the assembly causes a reversible alteration in the shape of the flexible intermediate section.

18. The spinal motion preservation assembly of claim 17 wherein the flexible intermediate section is a helical spring connecting the proximal bone anchor to the distal bone anchor.

19. The spinal motion preservation assembly of claim 18 wherein the helical spring is fabricated from a single piece of material.

20. The spinal motion preservation assembly of claim 1 wherein:
- the proximal bone anchor has a set of internal threads accessible from the proximal end of the proximal bone anchor; and
- the spinal motion preservation assembly has a threaded cap that engages the internal threads of the proximal bone anchor such that the threaded cap may be rotated relative to the proximal bone anchor to move distally and increase an intervertebral distance between the proximal vertebral body engaged with the proximal bone anchor and the distal vertebral body engaged with the distal bone anchor.

21. A spinal motion preservation assembly adapted for use in a spinal motion segment the spinal motion preservation assembly comprising:
  a distal bone anchor comprising:
    a distal end;
    a proximal end;
    a cavity in an interior of the distal bone anchor accessible from the proximal end, the cavity adapted for receipt of a corresponding portion of a driver tool; and
    a set of threads on an exterior of the distal bone anchor, the set of threads adapted to engage a distal vertebral body in the spinal motion segment;
  a pivot comprising:
    a distal end;
    a proximal end; and
    a middle between the distal end and the proximal end;
  a distal pivot cup comprising:
    an exterior corresponding to a portion of the cavity in the interior of the distal bone anchor; and
    a cavity at the proximal end of the distal pivot cup for receiving the distal end of the pivot;
  a proximal bone anchor comprising:
    a distal end;
    a proximal end;
    a cavity that runs through the interior of the proximal bone anchor from the distal end to the proximal end, the cavity adapted for receipt of a corresponding portion of a driver tool; and
    a set of threads on the exterior of the proximal bone anchor adapted to engage a proximal vertebral body in the motion segment;
  a proximal pivot cup comprising:
    a distal end;
    a proximal end; and
    a cavity at the distal end of the proximal pivot cup for receiving the proximal end of the pivot; and
  at least one component located between the distal end of the distal bone anchor and the proximal end of the proximal bone anchor that is elastically deformable;
  the distal bone anchor and the proximal bone anchor adapted for simultaneous delivery by a single driver tool wherein:
  the major diameter of the set of threads on the exterior of the distal bone anchor is less than the major diameter of the set of threads on the exterior of the proximal bone anchor;
  the handedness of the set of threads on the exterior of the distal bone anchor is the same as the handedness on the set of threads on the proximal bone anchor; and
  the pitch of the set of threads on the exterior of the distal bone anchor is finer than the set of threads on the proximal bone anchor such that rotation of the distal bone anchor and the proximal bone anchor at the same time and at the same rate by the driver tool will cause the distal vertebral body engaged with the distal bone anchor to move relative to a proximal vertebral body engaged with the proximal bone anchor to distract an intervertebral disc space between the distal vertebral body and the proximal vertebral body.

22. A spinal motion preservation assembly adapted for use in a spinal motion segment the spinal motion preservation assembly comprising:
  a distal bone anchor comprising:
    a distal end;
    a proximal end;
    a cavity in an interior of the distal bone anchor accessible from the proximal end, the cavity adapted for receipt of a corresponding portion of a driver tool; and
    a set of threads on an exterior of the distal bone anchor, the set of threads adapted to engage a distal vertebral body in the spinal motion segment;
  a pivot comprising:
    a distal end;
    a proximal end; and
    a middle between the distal end and the proximal end;
  a distal pivot cup comprising:
    an exterior corresponding to a portion of the cavity in the interior of the distal bone anchor; and
    a cavity at the proximal end of the distal pivot cup for receiving the distal end of the pivot;
  a proximal bone anchor comprising:
    a distal end;
    a proximal end;
    a cavity that runs through the interior of the proximal bone anchor from the distal end to the proximal end, the cavity adapted for receipt of a corresponding portion of a driver tool; and
    a set of threads on the exterior of the proximal bone anchor adapted to engage a proximal vertebral body in the motion segment;
  a proximal pivot cup comprising:
    a distal end;
    a proximal end; and
    a cavity at the distal end of the proximal pivot cup for receiving the proximal end of the pivot; and
  at least one component located between the distal end of the distal bone anchor and the proximal end of the proximal bone anchor that is elastically deformable;
  the distal bone anchor and the proximal bone anchor adapted for simultaneous delivery by a single driver tool wherein:
  the distal bone anchor and the proximal bone anchor can be retained by the single driver tool so that both the distal bone anchor and the proximal bone anchor while retained on the driver tool can be axially advanced into the spinal motion segment as the driver tool maintains the relative position of the distal bone anchor to the proximal bone anchor so that the proximal bone anchor is provided to the proximal vertebral body via timed delivery to engage a helical thread path in the proximal vertebral body previously cut by the passage of the distal vertebral bone anchor.

* * * * *

UNITED STATES PATENT AND TRADEMARK OFFICE
CERTIFICATE OF CORRECTION

PATENT NO.        : 7,601,171 B2                                      Page 1 of 1
APPLICATION NO.   : 11/256810
DATED             : October 13, 2009
INVENTOR(S)       : Ainsworth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 739 days.

Signed and Sealed this

Fifth Day of October, 2010

David J. Kappos
*Director of the United States Patent and Trademark Office*